US011034732B2

(12) United States Patent
Vandenberghe et al.

(10) Patent No.: US 11,034,732 B2
(45) Date of Patent: Jun. 15, 2021

(54) METHODS AND COMPOSITIONS FOR MODIFYING ASSEMBLY-ACTIVATING PROTEIN (AAP)-DEPENDENCE OF VIRUSES

(71) Applicants: Massachusetts Eye and Ear Infirmary, Boston, MA (US); The Schepens Eye Research Institute, Inc., Boston, MA (US)

(72) Inventors: Luk H. Vandenberghe, Weston, MA (US); Anna Claire Maurer, Boston, MA (US)

(73) Assignees: Massachusetts Eye and Ear Infirmary, Boston, MA (US); The Schepens Eye Research Institute, Inc., Boston, MA (US)

(*) Notice: Subject to any disclaimer, the term of this patent is extended or adjusted under 35 U.S.C. 154(b) by 0 days.

(21) Appl. No.: 16/409,317

(22) Filed: May 10, 2019

(65) Prior Publication Data
US 2019/0330278 A1 Oct. 31, 2019

Related U.S. Application Data

(63) Continuation of application No. PCT/US2018/032166, filed on May 10, 2018.

(60) Provisional application No. 62/669,901, filed on May 10, 2018, provisional application No. 62/504,318, filed on May 10, 2017.

(51) Int. Cl.
*C07K 14/015* (2006.01)
*C12N 15/86* (2006.01)

(52) U.S. Cl.
CPC ............ *C07K 14/015* (2013.01); *C12N 15/86* (2013.01); *C12N 2750/14122* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| 5,037,384 | A | 8/1991 | Chang |
| 7,906,111 | B2 | 3/2011 | Wilson et al. |
| 2004/0216750 | A1 | 11/2004 | Snyder et al. |
| 2007/0028928 | A1 | 2/2007 | Peyman |
| 2016/0215024 | A1 | 7/2016 | Vandenberghe et al. |
| 2017/0028082 | A1 | 2/2017 | Wilson et al. |
| 2017/0096683 | A1 | 4/2017 | Scaria et al. |

FOREIGN PATENT DOCUMENTS

| CA | 2193802 | 1/1996 |
| JP | 2007-500518 | 1/2007 |
| WO | WO 2005/033321 | 4/2005 |
| WO | WO 2006/110689 | 10/2006 |
| WO | WO 2014/160092 | 10/2014 |
| WO | WO 2015/054653 | 4/2015 |
| WO | WO 2016/144892 | 9/2016 |
| WO | WO 2017/019994 | 2/2017 |

OTHER PUBLICATIONS

Adachi et al., "MOLPHY: Programs for Molecular Phylogenetics based on Maximum Likelihood," Tokyo Institute of Statistical Mathematics, 1996, ed.
Altschul et al., "Gapped BLAST and PSI-BLAST: A new generation of protein database search programs," Nucleic Acids Res., 1997, 25:3389 3402.
American Society of Gene & Cell Therapy 17th Annual Meeting, Molecular Therapy, May 1, 2014, 22(Supplement 1): S1-S305.
Anisimova et al., "Approximate likelihood-ratio test for branches: A fast, accurate, and powerful alternative," Systematic Biology, 2006, 55:539-52.
AU Office Action in Australian Appln. No. 2016256894, dated Dec. 13, 2019, 3 pages.
Ausar et al., "Conformational stability and disassembly of Norwalk virus-like panicles. Effect of pH and temperature," J. Biol. Chem., 2006, 281:19478-88.
Balazs et al., "Antibody-based protection against HIV infection by vectored immunoprophylaxis," Nature, 2012, 481:81-4.
Balazs et al., "Broad protection against influenza infection by vectored immunoprophylaxis in mice," Nat. Biotechnol., 2013, 31:647-52.
Bartel et al., "Directed evolution of novel adeno-associated viruses for therapeutic gene delivery," Gene Therapy, Mar. 2012, 19: 694-700.
Boutin et al., 2010, "Prevalence of serum IgG and neutralizing factors against AAV types 1, 2, 5, 6, 8 and 9 in the healthy population: implications for gene therapy using AAV vectors," Hum. Gene Ther., 21:704-12.
Calcedo et al. "Worldwide Epidemiology of Neutralizing Antibodies to Adeno-Associated Viruses," J. Infect. Dis., 2009, 1199:381-90.
Cao et al., "Phylogenetic relationships among eutherian orders estimated from inferred sequences of mitochondrial proteins: instability of a tree based on a single gene," J. Mol. Evol., 1994, 39:519-27.
Carvalho et al., "Abstract #: 120: Retinal Tropism of In Silico Reconstructed Ancestral Adeno-Associated Viruses," Molecular Therapy, May 2014, 22(Supplement 1): S45.
Darriba et al., "ProTest3: Fast selection of best-fit models of protein evolution," Bioinfonnatics, 2011, 27(8):1164-5.
Dayhoff et al., "22 a model of evolutionary change in proteins." Atlas of protein sequence and structure. vol. 5. National Biomedical Research Foundation Silver Spring, 1978, 345-352.
Deal et al., "Vectored antibody gene delivery protects against plasmodium falciparum sporozoite challenge in mice," PNAS USA, 2014, 111:12528-32.
DiMattia et al., "Structural insight into the unique properties of adeno-associated virus serotype 9," Journal of Virology, Jun. 15, 2012, 86(12):6947-58.
EBI Accession No. GSP:ANJ81137, "Adeno-associated viral capsid protein, AAV-8," Dec. 13, 2007.

(Continued)

*Primary Examiner* — Stacy B Chen
(74) *Attorney, Agent, or Firm* — Fish & Richardson P.C.

(57) ABSTRACT

Methods and compositions are provided that can be used to modify the assembly activating protein (AAP)-dependence of an adeno-associated virus (AAV).

14 Claims, 13 Drawing Sheets
(10 of 13 Drawing Sheet(s) Filed in Color)
Specification includes a Sequence Listing.

(56) References Cited

OTHER PUBLICATIONS

Edgar, "MUSCLE: A multipole sequence alignment method with reduced time and space complexity," BMC Bioinform., 2004, 5:113.
EP European Search Report in Application No. 16790158.6, dated Jan. 3, 2019, 5 pages.
EP European Search Report in Application No. 18190809.6, dated Dec. 19, 2018, 5 pages.
EP Extended European Search Report in Application No. 168311443.3, dated Nov. 26, 2018, 20 pages.
Felsenstein, "Maximum Likelihood and Minimum-Steps Methods for Estimating Evolutionary Trees from Data on Discrete Characters," Systematic Biology, 1973, 22:240-9.
Fisher et al., "Recombinant adeno-associated virus for muscle directed gene therapy," 1997, Nature Med., 3:306-12.
Gao et al., "Adeno-associated viruses undergo substantial evolution in primates during natural infections," PNAS, 2003, 100:6081-6.
Gao et al., "Clades of Adeno-associated viruses are widely disseminated in human tissues," J. Virol., 2004, 78:6381-88.
Gao et al., "New recombinant serotypes of AAV vectors," Current Gene Ther., 2005, 5:285-97.
Gascuel, "BioNJ: An improved version of the NJ algorithm based on a simple model of sequence data," Mol. Biol. Evol., 1997, 14:685-95.
GenBank Accession No. AAC03780.1, "major coat protein VP1 [Adeno-associated virus-2]," Feb. 24, 1998, 1 page.
GenBank Accession No. AAD13756.1, "capsid protein [Adeno-associated virus-5]," Feb. 10, 1999, 1 page.
GenBank Accession No. AAD27757,1, "capsid protein [Adeno-associated virus—1]," Apr. 27, 1999. 1 page.
GenBank Accession No. AAN03857.1, "capsid protein [Adeno-associated virus—8]," Sep. 2, 2002, 1 pages.
GenBank Accession No. AA088201.1, "capsid protein [Non-human primate Adeno-associated virus]," Apr. 9, 2003, 1 page.
GenBank Accession No. AAS99264.1, "capsid protein VP1 [Adeno-associated virus 9]," May 25, 2004, 1 page.
GenBank Accession No. EU368910.1, "Adeno-associated virus isolate AAV6.2 capsid protein VP1 gene, partial cds," Jul. 31, 2008, 1 page.
GenBank Accession No. EU368926, "Adeno-associated virus isolate rh32.33 capsid protein VP1 gene, partial cds," Jul. 31, 2008, 1 page.
Guindon et al., "New algorithms and methods to estimate maximum-likelihood phylogenies: assessing the performance of PhyML 3.0," System. Biol., 2010, 59:307-21.
Guindon et al., "A simple, fast, and accurate algorithm to estimate large phylogenies by maximum likelihood," Systematic Biology, 2003, 52:696-704.
Henikoff et al., "Amino acid substitution matrices from protein blocks," PNAS, 1992, 89:10915-9.
Jones et al., "The rapid generation of mutation data matrices from protein sequences," 1992, Comp. Appl. Biosci., 8:275-82.
Katoh et al., "MAFFT version 5: Improvement in accuracy of multiple sequence alignment," Nuc. Acids Res., 2005, 33:511-8.
Koerber et al., "DNA Shuffling of Adeno-associated Virus Yields Functionally Diverse Viral Progeny," Molecular Therapy, Aug. 2008, 16: 1703-1709.
Lassmann et al., "Kalign, Kalignvu and Mumsa: Web servers for multiple sequence alignment," Nuc. Acids Res., 2006, 34:W596-99.
Limberis et al., "Intranasal antibody gene transfer in mice and ferrets elicits broad protection against pandemic influenza," Sci. Transl. Med., 2013, 5:187ra72.
Lock et al., "Rapid, simple, and versatile manufacturing of recombinant adeno-associated viral vectors at scale," Hum. Gene Ther, 2010, 21:1259-71.
Loytynoja et al., "An Algorithm for progressive multiple alignment of sequences with insertions," PNAS USA, 2005, 102:10557-62.
Loytynoja et al., "Phylogeny-Aware Gap Placement Prevents Errors in Sequence Alignment and Evolutionary Analysis," Science, 2008, 320:1632-5.
Maheshri et al., "Directed evolution of adeno-associated virus yields enhanced gene delivery vectors," Nature Biotechnology, Jan. 2006, 24: 198-204.
Manning et al., "Transient immunosuppression allows transgene expression following readministration of adeno-associated viral vectors," 1998, Human Gene Ther., 9:477-85.
Mao et al., "Persistent Suppression of Ocular Neovascularization with intravitreal administration of AAVrh.10 coding for Bevaciztumab," Hum. Gene Ther., 2011, 22:1525-35.
Nakai et al., "A limited number of transducible hepatocytes restricts a wide-range linear vector dose response in recombinant adeno-associated virus-mediated liver transduction," J. Virol., 2002, 76:11343-9.
Nakai et al., "Unrestricted hepatocyte transduction with adeno-associated virus serotype 8 vectors in 4 mice," J. Virol., 2005, 79:214-24.
Nam et al., "Structure of adeno-associated virus serotype 8, a gene therapy vector," Journal of Virology, Nov. 15, 2007, 81(22):12260-71.
Naumer et al., "Properties of the adeno-associated virus assembly-activating protein," Journal of Virology, Dec. 1, 2012, 86(23):13038-48.
Notredame et al., "T-Coffee: A novel method for fast and accurate multiple sequence alignment," J. Mol. Biol., 2000, 302:205-17.
Pacouret et al., "AAV-ID: a rapid and robust assay for batch-to-batch consistency evaluation of AAV preparations," Molecular Therapy, Jun. 7, 2017, 25(6):1375-86.
Paul et al., "Determination of hepatitis E virus seroprevalence by using recombinant fusion proteins and synthetic peptides," 1994, J. Infect. Dis., 169:801-6.
PCT International Preliminary Report on Patentability in International Application No. PCT/US2016/031218, dated Nov. 16, 2017, 7 pages.
PCT International Preliminary Report on Patentability in international Application No. PCT/US2016/032166, dated Nov. 12, 2019, 8 pages.
PCT International Preliminary Report on Patentability in International Application No. PCT/US2016/044819, dated Feb. 8, 2018, 5 pages.
PCT international Search Report and Written Opinion in International Application No. PCT/US2014/060163, dated Jul. 13, 2015, 19 pages.
PCT International Search Report and Written Opinion in International Application No. PCT/US2016/031218, dated Aug. 8, 2016, 12 pages.
PCT International Search Report and Written Opinion in International Application No. PCT/US2016/044819, dated Oct. 31, 2016, 5 pages.
Pettersen et al., "UCSF Chimera—a visualization system for exploratory research and analysis," 2004, J. Comp. Chem., 25:1605-12.
Reeves, "Heterogeneity in the substitution process of amino acid sites of proteins coded for by mitochondrial DNA," 1992, J. Mol. Evol., 35:17-31.
Sakhria et al., "Co-Circulation of Toscana Virus and Punique Virus in Northern Tunisia: A microneutralisation-based seroprevalence study," PLOS Negl. Trop. Dis., 2013, 7:e2429.
Santiago-Ortiz et al., "AAV ancestral reconstruction library enables selection of broadly infectious viral variants," gene Therapy, Jul. 2015, 22: 934-946.
Sarkar et al., Abstract #: 194: "Seroprevalence Assessment of Novel, Ancestrally Derived AAV Vectors," Molecular Therapy, May 2014, 22(Supplement 1): S74.
Sauerbrei et al. "Seroprevalence of herpes simplex virus type 1 and type 2 in Thuringia, Germany, 1999 to 2006," Euro Survell., 2011 ,16(44):3).
Schneider et al., "Empirical codon substitution matrix," BMC Bioinform., 2005, 6:134.
Schon et al., "Retinal gene delivery by adeno-associated vines (AAV) vectors: Strategies and applications," European Journal of Pharmaceutics and Biopharmaceutics. Jan. 2015, 95: 343-352.
Schuster et al., "Biodistribution of adeno-associated virus serotype 9 (AAV9) vector after intrathecal and intravenous delivery in mouse," Frontiers in Neuroanatomy, Jun. 2014, 8: 42 (14 pages).

(56) References Cited

OTHER PUBLICATIONS

Schwarz, "Estimating the Dimension of a Model," Ann. Statist. 1978, 6:461-4.

Sonntag et al., "The assembly-activating protein promotes capsid assembly of different adeno-associated virus serotypes," Journal of Virology, Dec. 1, 2011, 85(23):12686-97.

Thompson et al., "CLUSTAL W: improving the sensitivity of progressive multiple sequence alignment through sequence weighting, position-specific gap penalties and weight matrix choice," Nuc. Acids Res., 1994, 22:4673-90.

Wang et al., "Systematic Evaluation of AAV Vectors for Liver directed Gene Transfer in Murine Models," Mol. Ther, 2010, 18:118-25.

Watanabe et al., "AAVrh10-mediated genetic delivery of bevacizumab to the pleura to provide local anti-VEGF to suppress growth of metastatic lung tumors," Gene Ther., 2010, 17:1042-51.

Whelan et al., "A general empirical model of protein evolution derived from multiple protein families using a maximum-likelihood approach," Mol. Biol. Evol., 2001, 18:691-9.

Xie et al., "AAV-mediated persistent bevacizurnab therapy suppresses tumor growth of ovarian cancer," Gynecol. Oncol, 2014, 135: 325-32.

Xu et al., "Seroprevalence of herpes simplex virus types 1 and 2 in pregnant women in the United States," Am. J. Obstet. Gynecol., 2007, 196:43,e1-6.

Yang, "PAML 4: phylogenetic analysis by maximum likelihood," Mol. Biol. Evol., 2007, 24:1586-91.

Yang, "Maximum-likelihood estimation of phylogeny from DNA sequences when substitution rates differ over sites," Mol. Biol. Evol., 1993, 10:1396-1401.

Yang, "PAML: A program package for phylogenetic analysis by maximum likelihood," Comp. Applic. BioSci., 1997, 13:555-6.

Zinn and Vandenberghe, "Adeno-associated virus: fit to serve," Current Opinion in Virology, Oct. 2014, 8: 90-97.

Zinn et al., "Abstract #: 237: In Silico, Ancestral Reconstruction of AAV Particles Circumvents Pre-Existing Immunity in Humans," Molecular Therapy, May 2014, 22(Supplement 1): S90.

Zinn et al., "In Silico Reconstruction of the Viral Evolutionary Lineage Yields a Potent Gene Therapy Vector," Cell reports, Aug. 2015, 12: 1056-1068.

AU Office Action in Australian Appln. No. 2019201986, dated Mar. 13, 2020, 7 pages.

CA Office Action in Canadian Application No. 2,927,077, dated Jul. 2, 2020, 3 pages.

IN Office Action in Indian Appln. No. 201637014659, dated May 28, 2020, 8 pages.

Sen et al., "Improved adeno-associated virus (AAV) serotype 1 and 5 vectors for gene therapy", Scientific Reports, May 2013, 3(1):1-6.

Maurer et al. "The Assembly-Activating Protein Promotes Stability and Interactions between AAV's Viral Proteins to Nucleate Capsid Assembly," Cell Rep., May 2018, 23:1817-1830.

PCT International Search Report and Written Opinion in International Appln. No. PCT/US2018/032166, dated Sep. 27, 2018, 12 pages.

EP Extended European Search Report in European Appln. No. 18799088.2, dated Feb. 26, 2021, 7 pages.

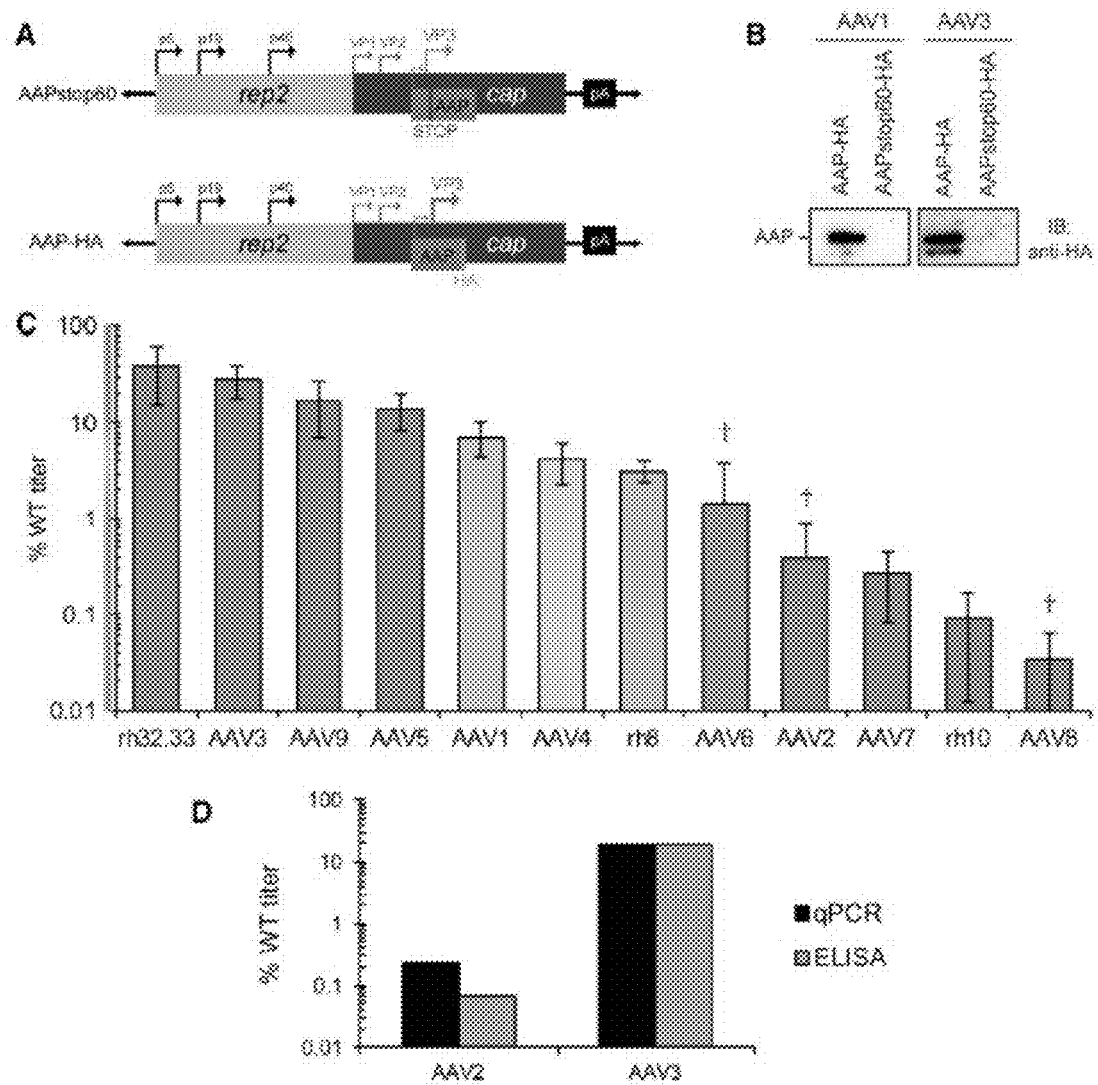
FIG. 1A-D

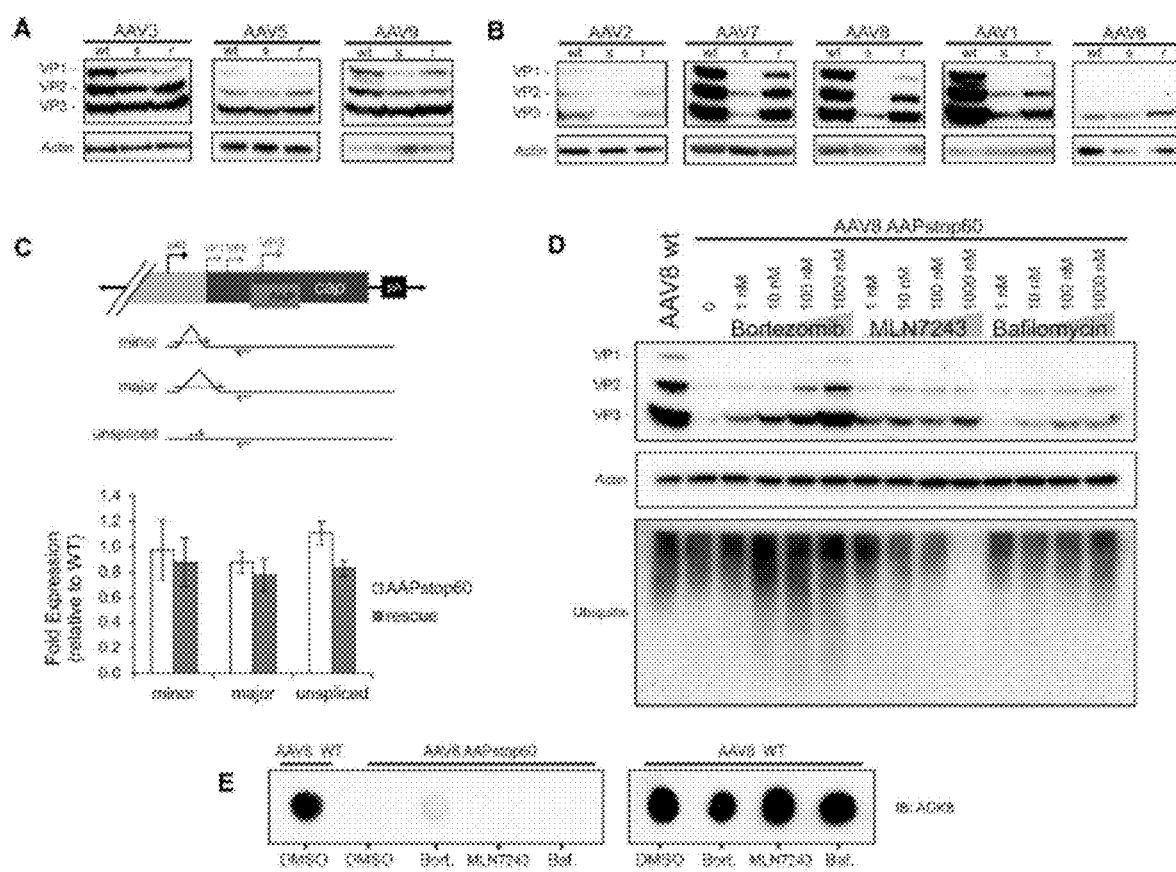
FIG. 2A-E

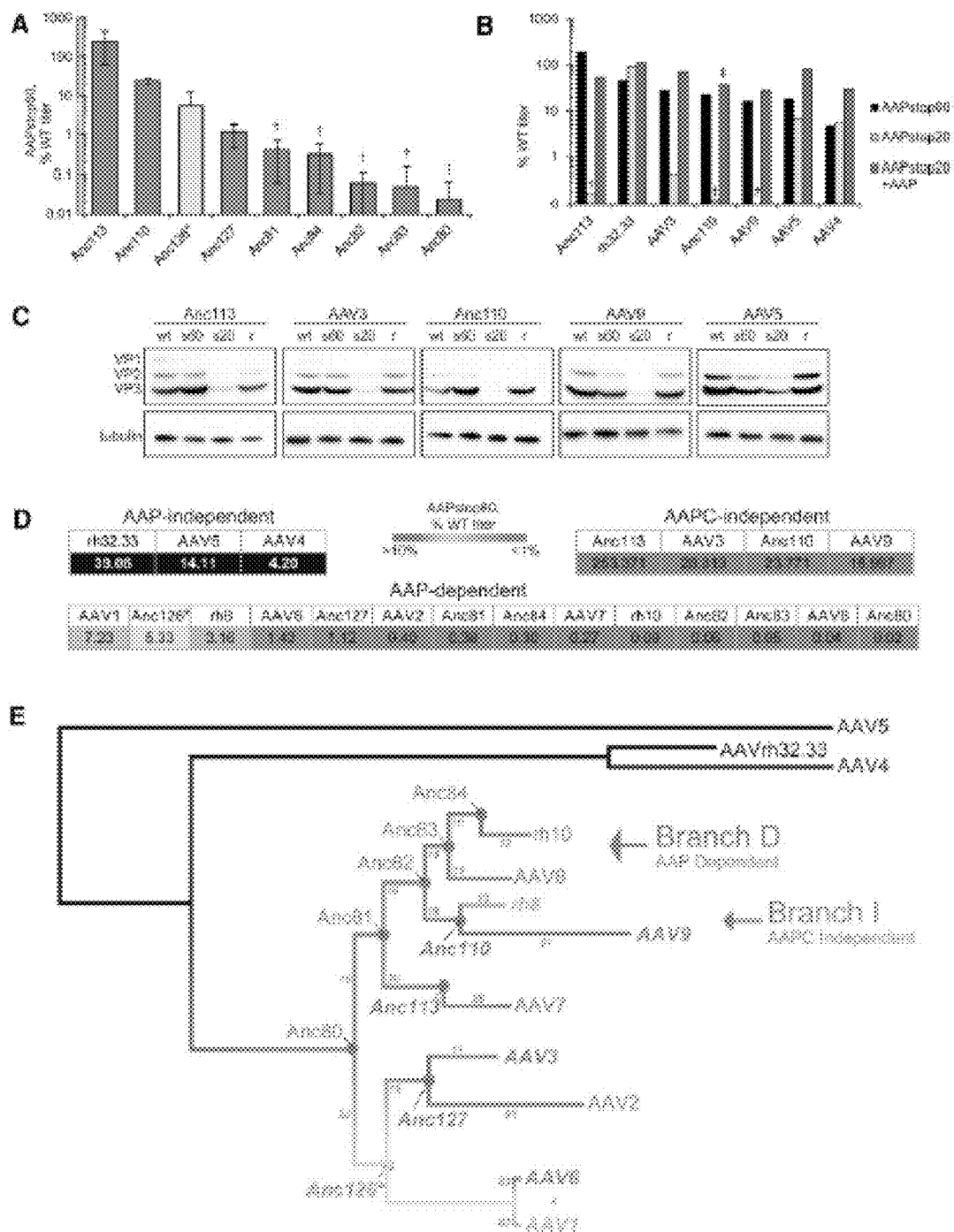
FIG. 3A-E

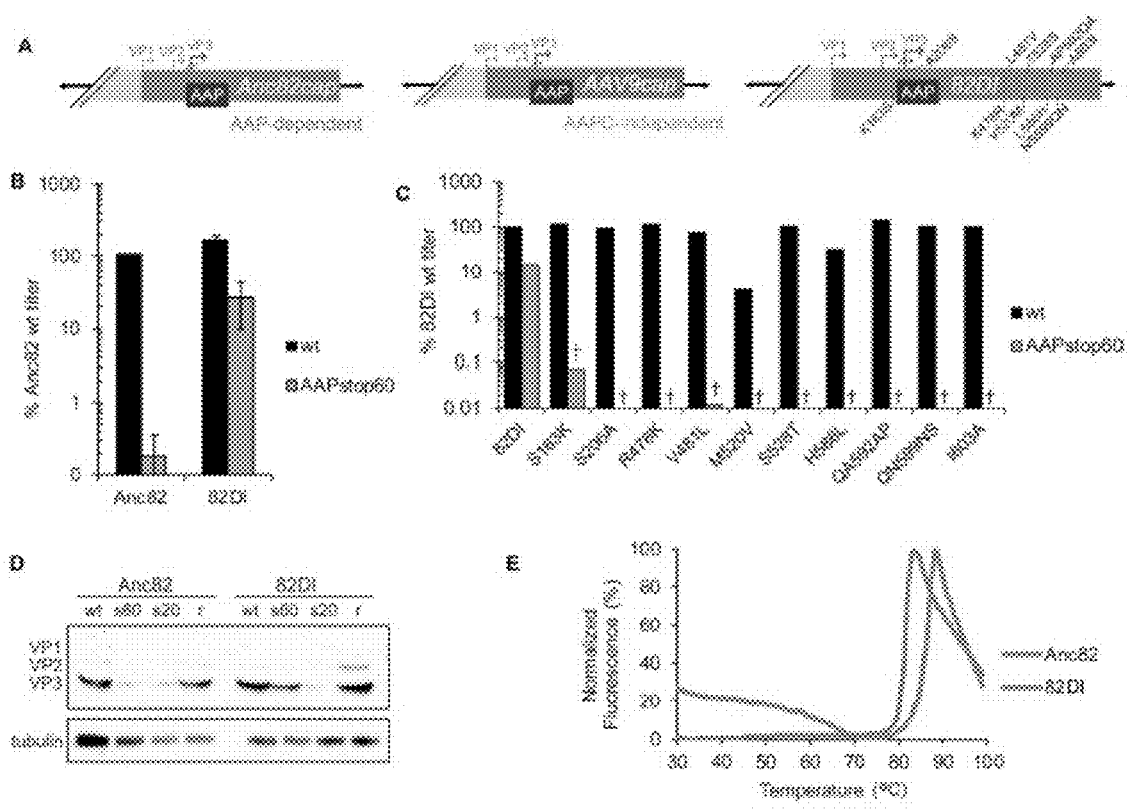
FIG. 4A-E

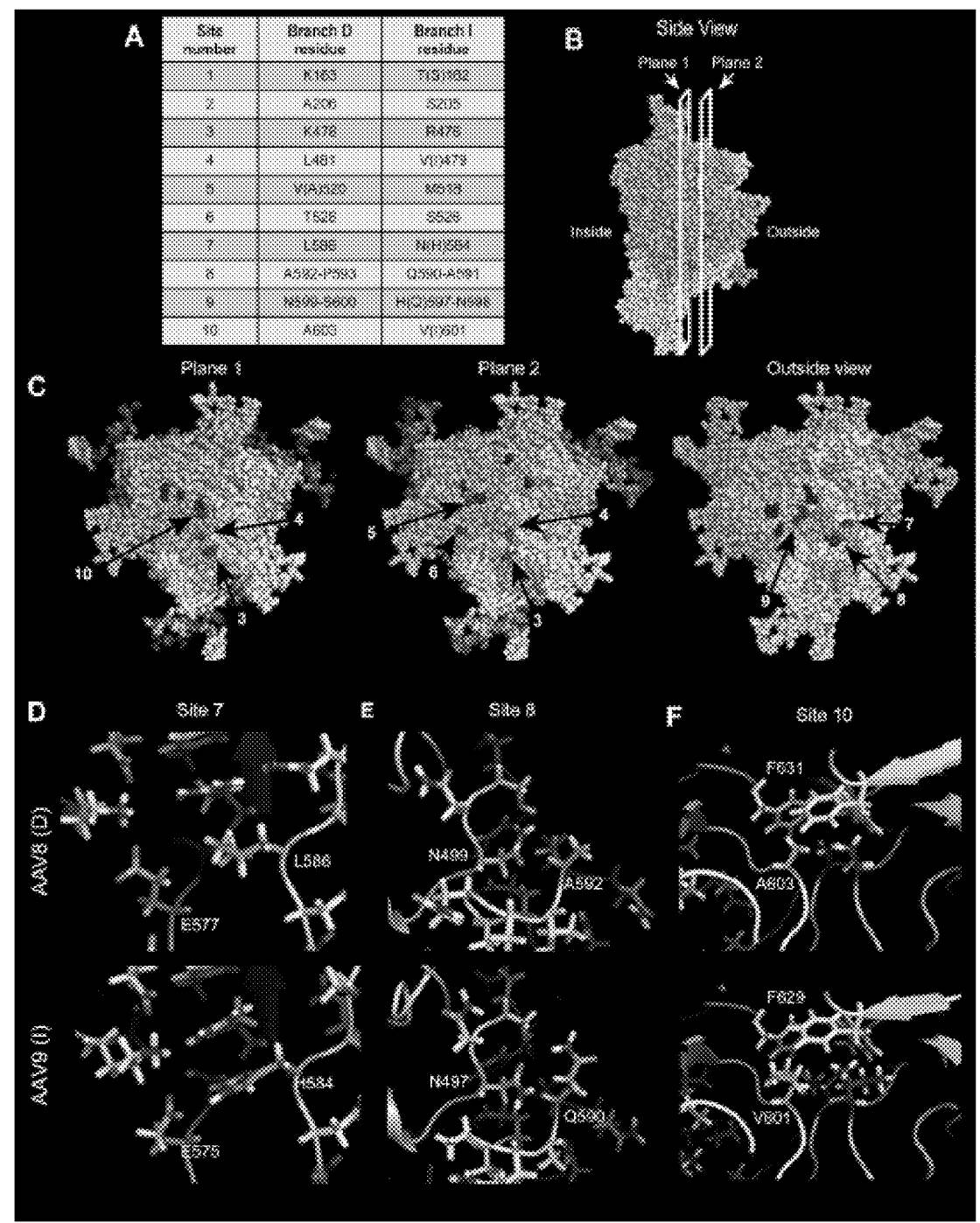
FIG. 5A-F

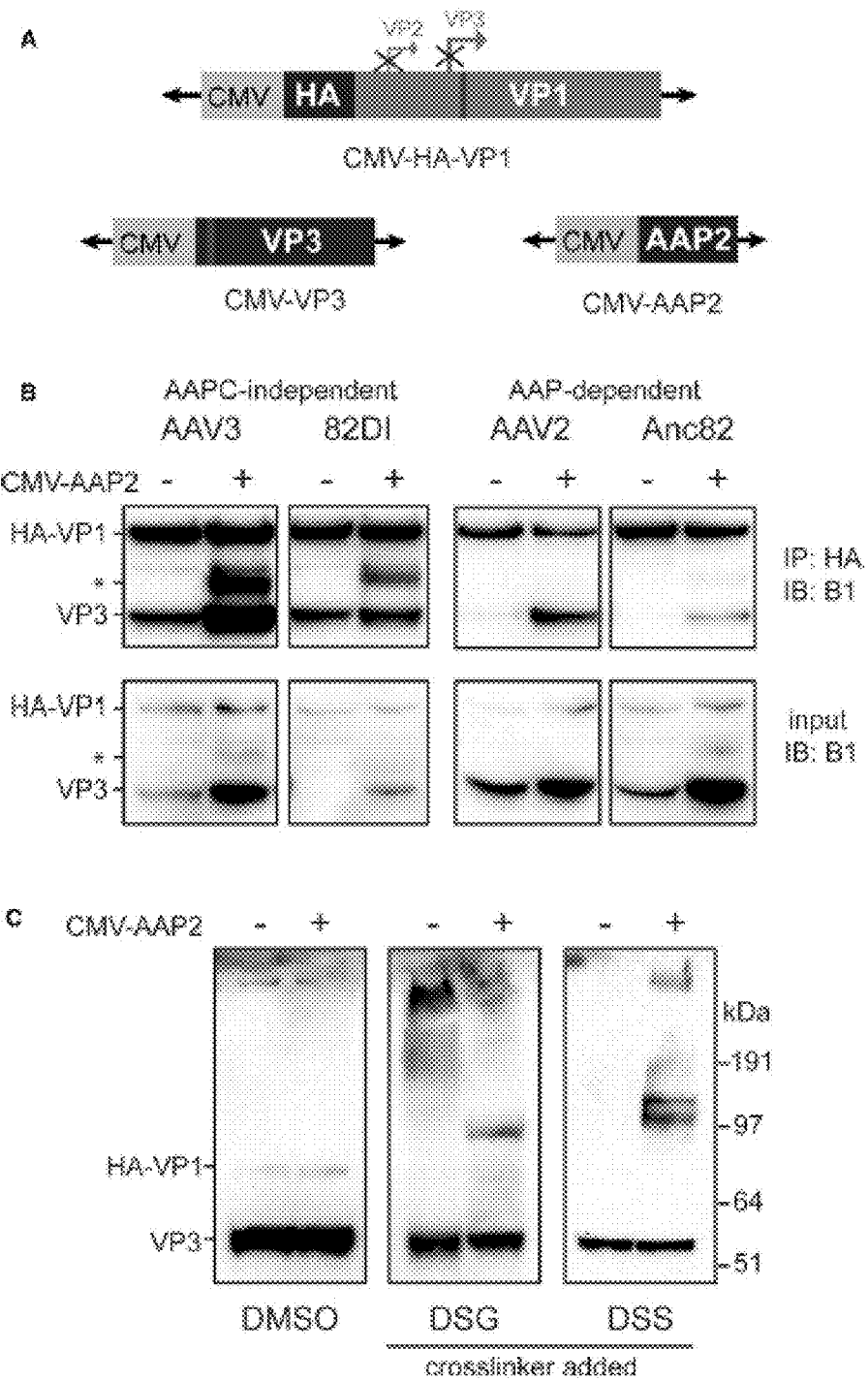
FIG. 6A-C

FIG. 8A-B

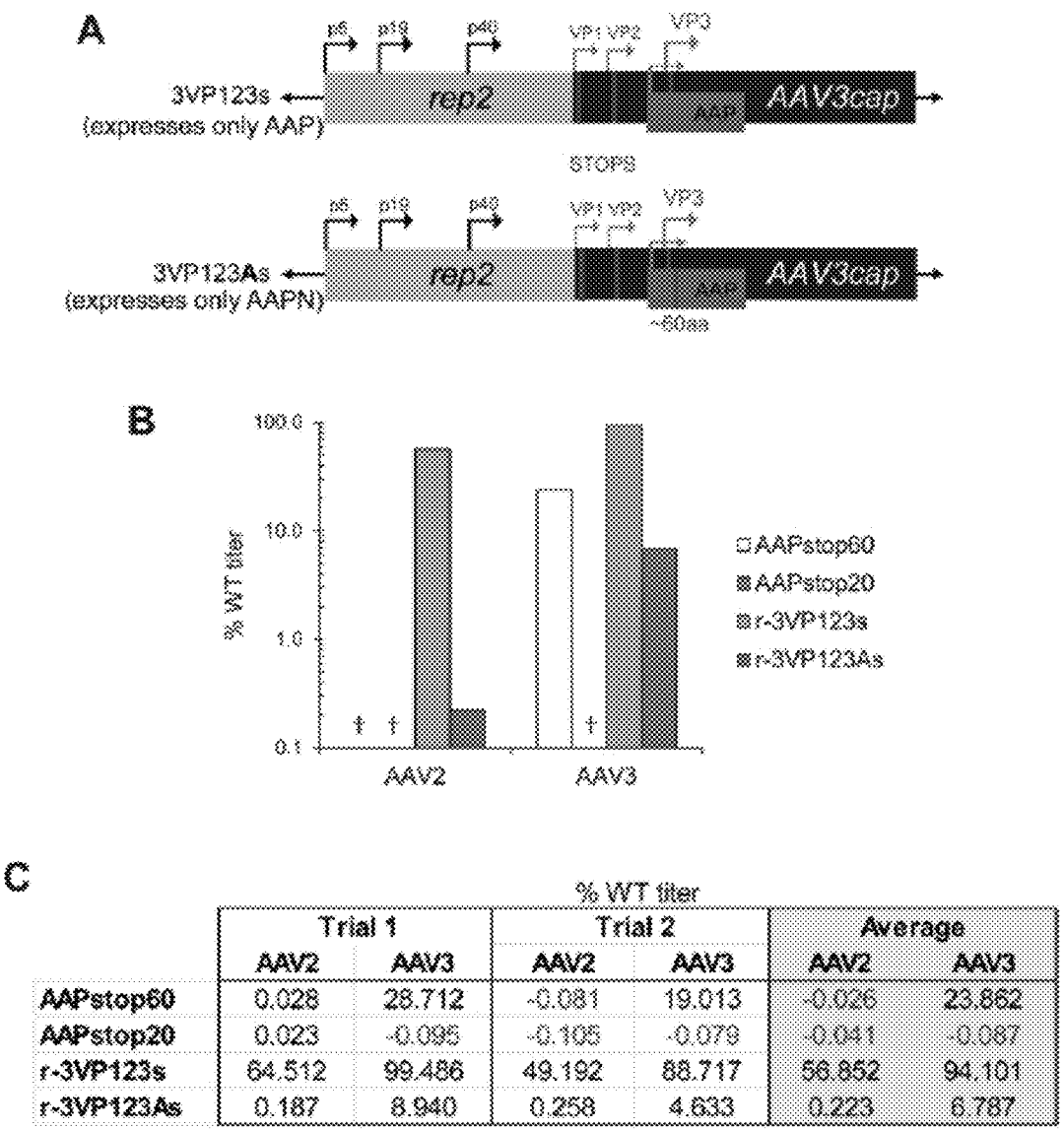
FIG. 10A-C

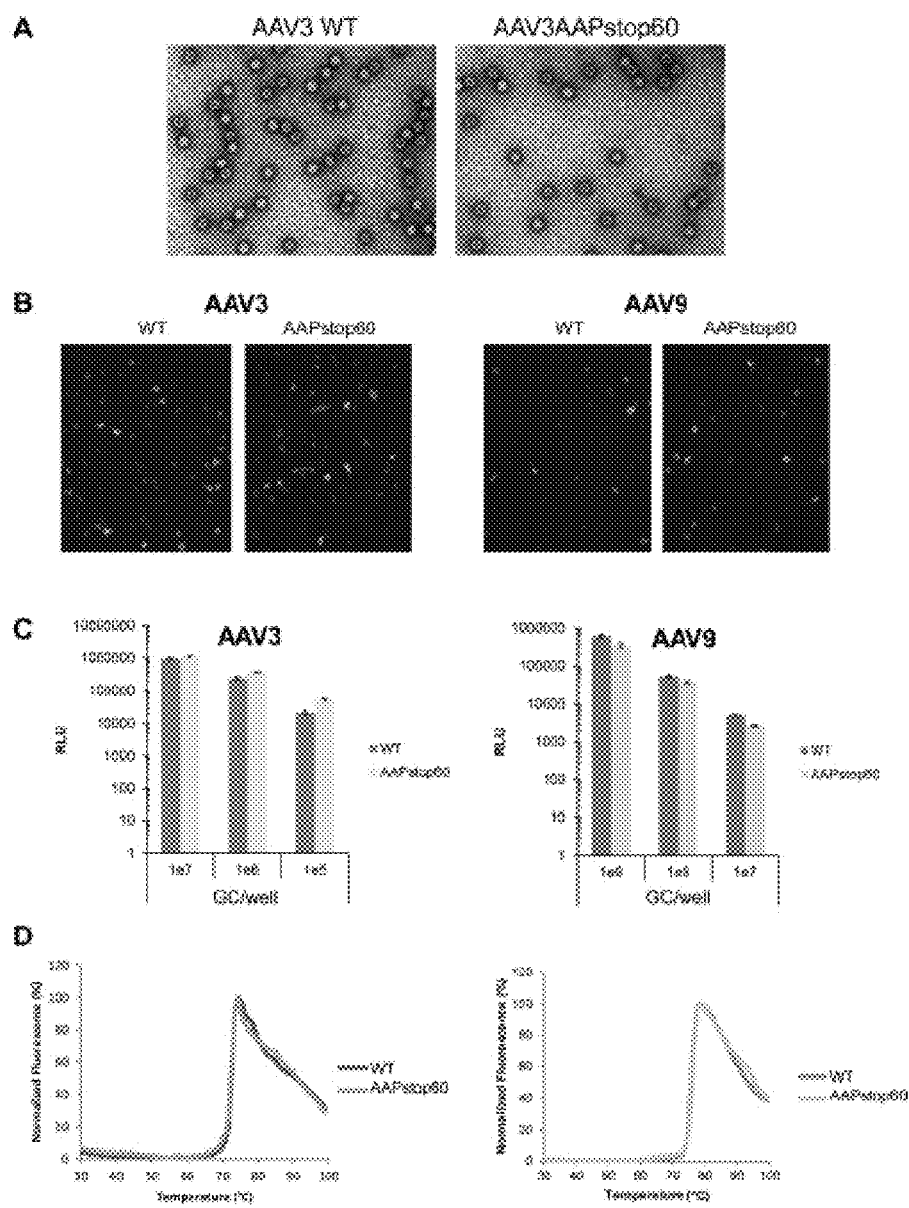
FIG. 11A-D

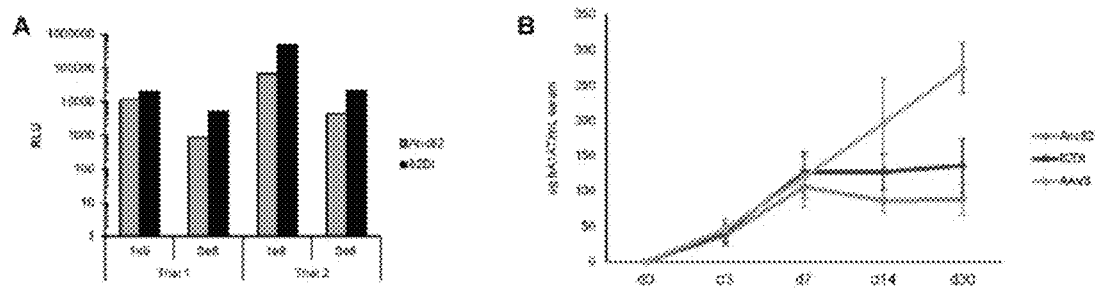
FIG. 12A-B
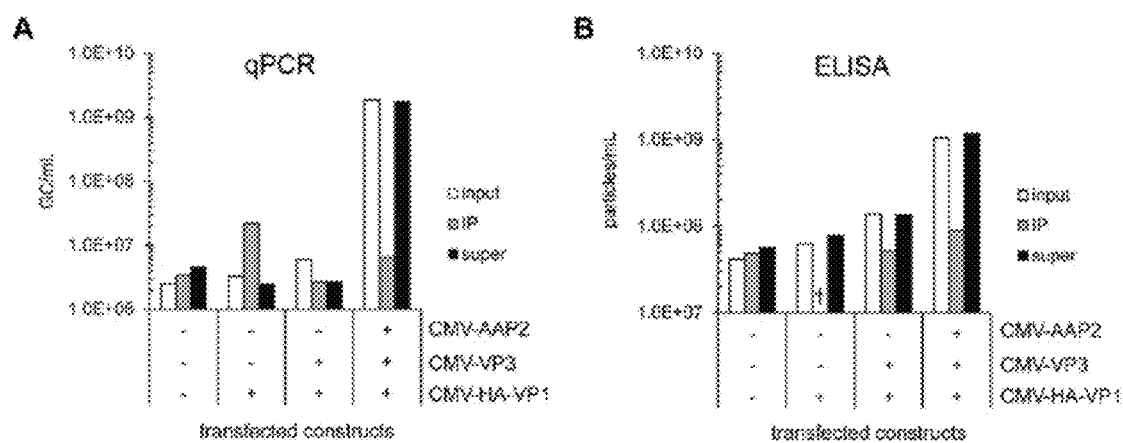
FIG. 13A-B

```
                        SEQUENCE LISTING

<160> NUMBER OF SEQ ID NOS: 4

<210> SEQ ID NO 1
<211> LENGTH: 738
<212> TYPE: PRT
<213> ORGANISM: Artificial Sequence
<220> FEATURE:
<223> OTHER INFORMATION: Synthetically-generated adeno-associated virus
      capsid protein

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Arg Glu Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Ser Asn Thr Met Ala Ala Gly Gly
        195                 200                 205

Gly Ala Pro Met Ala Asp Asn Asn Glu Gly Ala Asp Gly Val Gly Asn
```

```
                210                 215                 220
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Asn Phe Lys Leu Phe Asn
305                 310                 315                 320

Ile Gln Val Lys Glu Val Thr Thr Asn Glu Gly Thr Lys Thr Ile Ala
                325                 330                 335

Asn Asn Leu Thr Ser Thr Val Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
                370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Ser Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Thr Thr Gly Gly Thr Ala Gly Thr Gln Thr Leu Gln
                450                 455                 460

Phe Ser Gln Ala Gly Pro Ser Ser Met Ala Asn Gln Ala Lys Asn Trp
465                 470                 475                 480

Leu Pro Gly Pro Cys Tyr Arg Gln Gln Arg Val Ser Thr Thr Thr Asn
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Asp Arg Phe Phe Pro Ser Ser Gly Val Leu Ile
                530                 535                 540

Phe Gly Lys Gln Gly Ala Gly Asn Asp Asn Val Asp Tyr Ser Asn Val
545                 550                 555                 560

Met Ile Thr Ser Glu Glu Ile Lys Thr Thr Asn Pro Val Ala Thr
                565                 570                 575

Glu Glu Tyr Gly Val Val Ala Thr Asn Leu Gln Ser Ala Asn Thr Ala
                580                 585                 590

Pro Gln Thr Gly Thr Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640
```

Gly Leu Lys His Pro Pro Gln Ile Leu Ile Lys Asn Thr Pro Val
            645                 650                 655

Pro Ala Asp Pro Pro Thr Thr Phe Asn Gln Ala Lys Leu Asn Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 2
<211> LENGTH: 2217
<212> TYPE: DNA
<213> ORGANISM: Artificial Sequence
<220> FEATURE:
<223> OTHER INFORMATION: Nucleic acid encoding a synthetically-generated
      adeno-associated virus capsid protein

<400> SEQUENCE: 2

| | | | | | |
|---|---|---|---|---|---|
| atggctgccg | atggttatct | tccagattgg | ctcgaggaca | acctctctga | gggcattcgc | 60 |
| gagtggtggg | acctgaaacc | tggagccccg | aaacccaaag | ccaaccagca | aaagcaggac | 120 |
| gacggccggg | gtctggtgct | tcctggctac | aagtacctcg | acccttcaa | cggactcgac | 180 |
| aaggggagc | ccgtcaacgc | ggcggacgca | gcggccctcg | agcacgacaa | ggcctacgac | 240 |
| cagcagctca | aagcgggtga | caatccgtac | ctgcggtata | atcaccgcga | cgccgagttt | 300 |
| caggagcgtc | tgcaagaaga | tacgtctttt | gggggcaacc | tcgggcgagc | agtcttccag | 360 |
| gccaagaagc | gggttctcga | acctctcggt | ctggttgagg | aaggcgctaa | gacggctcct | 420 |
| ggaaagaaga | ggccggtaga | gcagtcacca | cagcgtgagc | ccgactcctc | cacgggcatc | 480 |
| ggcaagaaag | ccagcagcc | cgccaaaaag | agactcaatt | tcggtcagac | tggcgactca | 540 |
| gagtcagtcc | ccgaccctca | acctctcgga | gaacctccag | cagcgccctc | tggtgtggga | 600 |
| tctaatacaa | tggctgcagg | cggtggcgca | ccaatggcag | acaataacga | aggtgccgac | 660 |
| ggagtgggta | attcctcggg | aaattggcat | tgcgattcca | catggctggg | cgacagagtc | 720 |
| atcaccacca | gcacccgaac | ctgggccctg | cccacctaca | acaaccacct | ctacaagcaa | 780 |
| atctccaacg | gacctcggg | aggcagcacc | aacgacaaca | cctactttgg | ctacagcacc | 840 |
| ccctgggggt | attttgactt | taacagattc | cactgccact | ctcaccacg | tgactggcag | 900 |
| cgactcatca | caacaactg | gggattccgg | cccaagagac | tcaacttcaa | gctcttcaac | 960 |
| atccaggtca | agaggtcac | gacgaatgaa | ggcaccaaga | ccatcgccaa | taacctcacc | 1020 |
| agcaccgtcc | aggtgtttac | ggactcggaa | taccagctgc | cgtacgtcct | cggctctgcc | 1080 |
| caccagggct | gcctgcctcc | gttccggcg | gacgtcttca | tgattcctca | gtacggctac | 1140 |
| ctgactctca | caacggtag | tcaggccgtg | gacgttcct | ccttctactg | cctggagtac | 1200 |
| ttcccctctc | agatgctgag | aacgggcaac | aactttcaat | tcagctacac | tttcgaggac | 1260 |
| gtgccttcc | acagcagcta | cgcgcacagc | cagagtttgg | acaggctgat | gaatcctctc | 1320 |
| atcgaccagt | acctgtacta | cctgtcaaga | acccagacta | cggaggcac | agcgggaacc | 1380 |
| cagacgttgc | agttttctca | ggccgggcct | agcagcatgg | cgaatcaggc | caaaaactgg | 1440 |

```
ctgcctggac cctgctacag acagcagcgc gtctccacga caacgaatca aaacaacaac    1500
agcaactttg cctggactgg tgccaccaag tatcatctga acggcagaga ctctctggtg    1560
aatccgggcg tcgccatggc aacccacaag gacgacgagg accgcttctt cccatccagc    1620
ggcgtcctca tatttggcaa gcagggagct ggaaatgaca acgtggacta tagcaacgtg    1680
atgataacca gcgaggaaga aatcaagacc accaaccccg tggccacaga gagtatggc     1740 gtggtggcta ctaacctaca gtcggcaaac accgctcctc aaacggggac cgtcaacagc    1800
cagggagcct tacctggcat ggtctggcag aaccgggacg tgtacctgca gggtcctatt    1860
tgggccaaga ttcctcacac agatggcaac tttcacccgt ctcctttaat gggcggcttt    1920
ggacttaaac atccgcctcc tcagatcctc atcaaaaaca ctcctgttcc tgcggatcct    1980
ccaacaacgt tcaaccaggc caagctgaat tctttcatca cgcagtacag caccggacaa    2040
gtcagcgtgg agatcgagtg ggagctgcag aaggagaaca gcaagcgctg gaacccagag    2100
attcagtata cttccaacta ctacaaatct acaaatgtgg actttgctgt taatactgag    2160
ggtgtttact ctgagcctcg ccccattggc actcgttacc tcacccgtaa tctgtaa      2217
```

<210> SEQ ID NO 3
<211> LENGTH: 738
<212> TYPE: PRT
<213> ORGANISM: Artificial Sequence
<220> FEATURE:
<223> OTHER INFORMATION: Synthetically-generated adeno-associated virus
      capsid protein

<400> SEQUENCE: 3

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Arg Glu Pro Asp Ser Ser Thr Gly Ile
145                 150                 155                 160

Gly Lys Ser Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Ser Asn Thr Met Ala Ser Gly Gly
        195                 200                 205

Gly Ala Pro Met Ala Asp Asn Asn Glu Gly Ala Asp Gly Val Gly Asn
    210                 215                 220
```

```
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Asn Phe Lys Leu Phe Asn
305                 310                 315                 320

Ile Gln Val Lys Glu Val Thr Thr Asn Glu Gly Thr Lys Thr Ile Ala
            325                 330                 335

Asn Asn Leu Thr Ser Thr Val Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Ser Tyr
            405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Gly Thr Gln Thr Leu Gln
450                 455                 460

Phe Ser Gln Ala Gly Pro Ser Ser Met Ala Asn Gln Ala Arg Asn Trp
465                 470                 475                 480

Val Pro Gly Pro Cys Tyr Arg Gln Gln Arg Val Ser Thr Thr Thr Asn
            485                 490                 495

Gln Asn Asn Asn Ser Asn Phe Ala Trp Thr Gly Ala Thr Lys Tyr His
            500                 505                 510

Leu Asn Gly Arg Asp Ser Leu Met Asn Pro Gly Val Ala Met Ala Ser
        515                 520                 525

His Lys Asp Asp Glu Asp Arg Phe Phe Pro Ser Ser Gly Val Leu Ile
        530                 535                 540

Phe Gly Lys Gln Gly Ala Gly Asn Asp Asn Val Asp Tyr Ser Asn Val
545                 550                 555                 560

Met Ile Thr Ser Glu Glu Ile Lys Thr Thr Asn Pro Val Ala Thr
            565                 570                 575

Glu Glu Tyr Gly Val Val Ala Thr Asn His Gln Ser Ala Asn Thr Gln
            580                 585                 590

Ala Gln Thr Gly Thr Val Gln Asn Gln Gly Ile Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640
```

-continued

```
Gly Leu Lys His Pro Pro Gln Ile Leu Ile Lys Asn Thr Pro Val
            645                 650                 655

Pro Ala Asp Pro Pro Thr Thr Phe Asn Gln Ala Lys Leu Asn Ser Phe
        660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 4
<211> LENGTH: 2217
<212> TYPE: DNA
<213> ORGANISM: Artificial Sequence
<220> FEATURE:
<223> OTHER INFORMATION: Nucleic acid encoding a synthetically-generated
       adeno-associated virus capsid protein

<400> SEQUENCE: 4

| | |
|---|---|
| atggctgccg atggttatct tccagattgg ctcgaggaca acctctctga gggcattcgc | 60 |
| gagtggtggg acctgaaacc tggagccccg aacccaaag ccaaccagca aaagcaggac | 120 |
| gacggccggg tctggtgct tcctggctac aagtacctcg acccttcaa cggactcgac | 180 |
| aaggggagc ccgtcaacgc ggcggacgca gcggccctcg agcacgacaa ggcctacgac | 240 |
| cagcagctca aagcgggtga caatccgtac ctgcggtata tcacgccga cgccgagttt | 300 |
| caggagcgtc tgcaagaaga tacgtctttt gggggcaacc tcgggcgagc agtcttccag | 360 |
| gccaagaagc gggttctcga acctctcggt ctggttgagg aaggcgctaa gacggctcct | 420 |
| ggaaagaaga ggccggtaga gcagtcacca cagcgtgagc ccgactcctc cacgggcatc | 480 |
| ggcaagagcg ccagcagcc cgccaaaaag agactcaatt tcggtcagac tggcgactca | 540 |
| gagtcagtcc ccgaccctca acctctcgga gaacctccag cagcgccctc tggtgtggga | 600 |
| tctaatacaa tggcttcagg cggtggcgca ccaatggcag acaataacga aggtgccgac | 660 |
| ggagtgggta ttcctcggg aaattggcat tgcgattcca catggctagg cgacagagtc | 720 |
| atcaccacca gcacccgaac ctgggccctg cccacctaca acaaccccct ctacaagcaa | 780 |
| atctccaacg gaacctcggg aggcagcacc aacgacaaca cctactttgg ctacagcacc | 840 |
| ccctgggggt attttgactt taacagattc cactgccact tctcaccacg tgactggcag | 900 |
| cgactcatca caacaactg gggattccgg cccaagagac tcaacttcaa gctcttcaac | 960 |
| atccaggtca agaggtcac gacgaatgaa ggcaccaaga ccatcgccaa taacctcacc | 1020 |
| agcaccgtcc aggtgtttac ggactcggaa taccagctgc cgtacgtcct cggctctgcc | 1080 |
| caccagggct gcctgcctcc gttcccggcg gacgtcttca tgattcctca gtacggctac | 1140 |
| ctgactctca acaacggtag tcaggccgtg gacgttcct ccttctactg cctggagtac | 1200 |
| ttccctctc agatgctgag aacgggcaac aactttcaat tcagctacac tttcgaggac | 1260 |
| gtgcctttcc acagcagcta cgcgcacagc cagagtttgg acaggctgat gaatcctctc | 1320 |
| atcgaccagt acctgtacta cctgtcaaga acccagacta cggaggcac agcgggaacc | 1380 |
| cagacgttgc agttttctca ggccgggcct agcagcatgg cgaatcaggc cagaaactgg | 1440 |

```
                                                      -continued
gtgcctggac cctgctacag acagcagcgc gtctccacga caacgaatca aaacaacaac    1500
agcaactttg cctggactgg tgccaccaag tatcatctga acggcagaga ctctctgatg    1560
aatccgggcg tcgccatggc aagccacaag gacgacgagg accgcttctt cccatccagc    1620
ggcgtcctca tatttggcaa gcagggagct ggaaatgaca acgtggacta tagcaacgtg    1680
atgataacca gcgaggaaga aatcaagacc accaaccccg tggccacaga agagtatggc    1740
gtggtggcta ctaaccacca gtcggcaaac acccaggctc aaacggggac cgtccaaaac    1800
cagggaatct tacctggcat ggtctggcag aaccgggacg tgtacctgca gggtcctatt    1860
tgggccaaga ttcctcacac agatggcaac tttcacccgt ctcctttaat gggcggcttt    1920
ggacttaaac atccgcctcc tcagatcctc atcaaaaaca ctcctgttcc tgcggatcct    1980
ccaacaacgt tcaaccaggc caagctgaat tctttcatca cgcagtacag caccggacaa    2040
gtcagcgtgg agatcgagtg ggagctgcag aaggagaaca gcaagcgctg gaacccagag    2100
attcagtata cttccaacta ctacaaatct acaaatgtgg actttgctgt taatactgag    2160
ggtgtttact ctgagcctcg ccccattggc actcgttacc tcacccgtaa tctgtaa      2217
```

METHODS AND COMPOSITIONS FOR MODIFYING ASSEMBLY-ACTIVATING PROTEIN (AAP)-DEPENDENCE OF VIRUSES

CROSS-REFERENCE TO RELATED APPLICATIONS

This application is a continuation of International Patent Application No. PCT/US2018/032166, filed on May 10, 2018, which claims the benefit of priority under 35 U.S.C. § 119(e) of U.S. Application No. 62/669,901, filed on May 10, 2018, and U.S. Application No. 62/504,318, filed on May 10, 2017, all three of which are incorporated herein by reference in their entirety.

SEQUENCE LISTING

The instant application contains a Sequence Listing which has been submitted electronically in ASCII format and is hereby incorporated by reference in its entirety. Said ASCII copy, created on May 10, 2019, is named Sequence Listine.txt and is 19,481 bytes in size.

TECHNICAL FIELD

This disclosure generally relates to viral vector systems.

BACKGROUND

Adeno-associated virus (AAV) is a leading platform in therapeutic gene transfer, primarily for in vivo gene therapy approaches. While preclinical and clinical studies continue to demonstrate AAV's potential as a reagent for safe and efficient gene delivery to alleviate a number of diseases, a bottleneck to its broader application is the production of sufficient vector quantities to treat these patient populations.

SUMMARY

In general, this disclosure describes and demonstrates the utility of a particular sequence motif within an AAV capsid protein that enables the assembly-activating protein (AAP)-dependence of the AAV to be modified. Thus, this sequence motif can be used to address and alleviate at least one of the bottlenecks encountered in the production of virus vectors. In particular, this disclosure describes a minimal motif defined through a novel phenotype-to-phylogeny mapping method that can be used to modify the AAP-dependence of a virus. Briefly, a number of ancestral AAVs that have been developed (see, for example, WO 2015/054653 and WO 2017/019994, which are incorporated herein by reference in their entirety) were used to examine AAP dependence across a wide structural differential. This analysis allowed for the identification of a minimal motif that determines AAP dependency.

In one aspect, the disclosure features adeno-associated virus (AAV) capsid polypeptides including an amino acid sequence having at least 95% sequence identity (e.g., at least 99% sequence identity) to the amino acid sequence of SEQ ID NO: 3. In some embodiments, the AAV capsid polypeptide has the amino acid sequence of SEQ ID NO:3. In some embodiments, the AAV capsid polypeptides are encoded by the nucleic acid sequence of SEQ ID NO: 4. In some embodiments, the AAV capsid polypeptide has the amino acid sequence of SEQ ID NO: 1, but contains the amino acid residues at the indicated positions shown in Table 1 for "independence" or "dependence" with respect to AAP.

TABLE 1.

| | Motif for Modifying AAP-Dependence | |
| --- | --- | --- |
| Site | Residue identity and position in Anc80, Anc81, Anc82, Anc84, rh10 and AAV8 "Independence" | Aligns to this residue in Anc110, rh8, and AAV9 "Dependence" |
| 1 | K163 | T162 (S in AAV9) |
| 2 | A206 | S205 |
| 3 | K478 | R476 |
| 4 | L481 | V479 (I in AAV9) |
| 5 | V520 (A in AAV8) | M518 |
| 6 | T528 | S526 |
| 7 | L586 | N584 (H in AAV9) |
| 8 | A592 - P593 | Q590-A591 |
| 9 | N599 - S600 | H597 - N598 (QN in AAV9) |
| 10 | A603 | V601 (I in AAV9) |

This disclosure also features virus particles including any of the adeno-associated virus (AAV) capsid polypeptides described herein. Such virus particles can further include a transgene.

In another aspect, the disclosure features nucleic acid molecules including a nucleic acid sequence having at least 95% sequence identity (e.g., at least 99% sequence identity) to the nucleic acid sequence of SEQ ID NO: 4 and encoding an adeno-associated virus (AAV) capsid polypeptide. In some embodiments, the nucleic acid molecule has the nucleic acid sequence of SEQ ID NO:4. In some embodiments, the nucleic acid molecule encodes the amino acid sequence of SEQ ID NO: 3.

The disclosure also provides vectors including any of the nucleic acid molecules described herein, as well as host cells including any of the nucleic acid molecules and/or vectors described herein. In some embodiments, the host cell is a packaging cell.

In another aspect, the disclosure features packaging cells including a nucleic acid molecule encoding an adeno-associated virus (AAV) capsid polypeptide, wherein the AAV capsid polypeptide has at least 95% sequence identity to the amino acid sequence of SEQ ID NO: 3. In some embodiments, the packaging cell lacks the assembly activating protein (AAP).

In another aspect, the disclosure includes methods of reducing the assembly activating protein (AAP)-dependence of an adeno-associated virus (AAV). Such methods include providing an AAV having a capsid polypeptide that has at least 95% sequence identity to the amino acid sequence of SEQ ID NO: 3.

In yet another aspect, the disclosure features methods of relieving, at least partially, the assembly activating protein (AAP)-dependence of an adeno-associated virus (AAV), the method including: incorporating a capsid polypeptide into the AAV that has at least 95% sequence identity to the amino acid sequence of SEQ ID NO: 3.

In still another aspect, the disclosure provides methods of engineering an adeno-associated virus (AAV) to reduce its dependence on assembly activating protein (AAP), including: engineering an AAV that comprises a capsid polypeptide that has at least 95% sequence identity to the amino acid sequence of SEQ ID NO: 3.

Any of the methods described herein can further include culturing the adeno-associated virus (AAV) in the absence of the assembly activating protein (AAP). Any of the methods described herein further can include sequencing the engineered adeno-associated virus (AAV). Any of the methods described herein further can include comparing the assembly activating protein (AAP)-dependence of the engineered adeno-associated virus (AAV) relative to a non-engineered or wild type AAV. Any of the methods described herein further can include aligning the engineered adeno-associated virus (AAV) with the non-engineered or wild type AAV.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 1A-D are a series of schematic diagrams, gels, and bar graphs of data demonstrating that the requirement for AAP ranges broadly across all clades of AAV. Panel A are schematics of AAPstop60 and AAP-HA construct maps. Black arrows: transcription start sites at p5, p19, and p40 viral promoters. Grey arrows: cap gene product translation start codons. Early stop codon (red) introduced by site directed mutagenesis ~60 aa into the AAP ORF. HA tag (orange) inserted at a conserved BsiWI site near AAP C-terminus. Panel B is a photograph of a gel demonstrating that AAV1 and AAV3 AAP-HA constructs were generated in both WT AAP and AAPstop60 context. Lysates from transfected HEK293 cells were harvested after 36 h, clarified by centrifugation, and interrogated for AAP by Western Blot with anti-HA antibody. Panel C is a graph demonstrating the vector produced from WT or AAPstop60 rep-cap constructs was titrated by qPCR to quantify DNase resistant particles. AAPstop60 titers are reported as a percentage of each WT serotype titer and represent the average of at least 3 independent experiments±SEM. Bar color corresponds to heatmap color on y-axis. † AAPstop60 titer below background level for at least one trial (no cap gene control). See Table 2 for statistics. Panel D is a graph of vector produced from WT and AAPstop60 constructs of AAV2 and AAV3 were titrated by A20 capsid ELISA, reported as a percentage of WT titer (average of two experiments; see also FIG. 11).

FIGS. 2A-E are a series of gels and graphs of experimental data showing VP protein levels in natural serotypes. HEK 293 cells were transfected with helper and rep-cap plasmids as denoted above the lane: (wt) WT AAP; (s) AAPstop60; (r) AAPstop60 plus a CMV-driven AAP2. Whole cell lysates were harvested after 36 hours, clarified by centrifugation, and VP levels interrogated with B1 antibody (VP1/2/3). Actin was used as a loading control. Serotypes of rep-cap plasmids indicated above each blot, with (Panel A) AAPstop60 titers ≥10% WT titer and (Panel B) AAPstop60 titers <10% WT titer. Panel C is a blot showing RNA quantified from AAV2 transfections as above, normalized to GAPDH, reported relative to AAV2 WT. Minor and major splice isoforms, as well as unspliced transcript levels, were examined as denoted on x-axis and diagrammed at right; primers indicated by arrows. Graph represents the mean of three independent experiments±SEM; there is no statistically significant difference between groups (see Table 2 for statistics). Panel D are blots of HEK 293 cells transfected with helper and AAV8 WT or AAPstop60 rep-cap plasmids as indicated. At 24 h, AAPstop60 transfected cells were treated with concentrations of Bortezomib, MLN7243, or Bafilomycin as indicated above lanes, and incubated an additional 8 h before whole cell lysates were harvested as in (Panel A) and (Panel B). VP levels were interrogated by Western Blot with B1 antibody (top). Blot was stripped and reprobed for Ubiquitin (bottom). Actin was used as a loading control (middle). Panel E are dot blots using lysates from Panel D treated with DMSO or 1 µM Bortezomib, MLN7243, or Bafilomycin as listed below were assayed for the presence of assembled capsids by dot blot with the ADK8 antibody (recognizes a conformational epitope only present in assembled AAV8 capsids). The experiment was repeated in the presence of AAP to control for any effects of the drugs on capsid assembly (right panel). See also FIG. 8.

FIGS. 3A-E are a series of gels, charts, and schematics representing experimental data demonstrating that the requirement for AAP exhibits branch specificity in the context of a putative AAV phylogeny. Panel A is a graph showing that AAPstop60s were generated for the nine putative ancestral AAVs. Vector produced from WT or AAPstop60 rep-cap constructs was titrated by qPCR to quantify DNase resistant particles. AAPstop60 titers are reported as a percentage of each serotype's WT titer and represent the mean of at least 3 independent experiments±SEM. Bar color corresponds to heatmap color on y-axis and is used also in (Panel D) and (Panel E). † AAPstop60 titer below background (no cap gene control) for at least one trial. See Table 2 for statistics. * Anc126 produces at consistently low titers (below 1e9 GC/mL) for WT and AAPstop60. Panel B is a graph showing that AAPstop20s were generated for AAV4 and all AAV variants with AAPstop60 titers ≥10% by introducing early stop codons at ~20 aa into the AAP ORF. Vector was produced and titrated as in Panel A, adding the AAPstop20 condition (light grey bars) and AAPstop20 plus a CMV-driven construct expressing a homologous AAP (dark grey bars) (mean of two experiments). † Titer below background (no cap gene control) for at least one trial. ‡ Rescue performed with AAP2. Panel C are gels of HEK 293 cells transfected with helper and rep-cap plasmids as denoted above lane: (wt) WT AAP; (s60) AAPstop60; (s20) AAPstop20; (r) AAPstop20 plus CMV-driven homologous AAP. Whole cell lysates were harvested after 36 hours and VP levels interrogated by Western Blot. Tubulin was used as a loading control. Panel D is the categorization of AAP phenotypes. Boxes below each serotype indicate AAPstop60 percentage of WT titer. Black boxes indicate AAP-independent (AAPstop20 titer is >>1%). Serotypes with AAPstop60 titers >10% (green) indicate assembly in absence of C-terminal two-thirds of AAP (AAPC-independent). Panel E is a reconstructed AAV phylogeny, branches colored as in Panel D. Grey numbers on branches indicate number of divergent amino acids between the two serotypes flanking the branch segment. See also FIGS. 8, 9, 10, and 12.

FIGS. 4A-F are a series of schematics, graphs, and gels experimental data showing the characterization of 82DI, an AAPC-independent gain-of-function mutant. Panel A are schematics of 82DI generated by introducing Branch I residue identities into an Anc82 rep-cap plasmid by site directed mutagenesis. Panel B is a graph of vector produced from Anc82, 82DI, and their AAPstop60s was titrated by quantifying DNase resistant particles (DRP), and is reported as a percentage of Anc82 WT titer. Graph represents the mean of four independent experiments, ±SEM. See Table 2 for statistics. Panel C is a graph, where each site in 82DI and 82DIAAPstop60 was reverted to its Anc82 identity individually by site directed mutagenesis. Vector titers quantifying DRPs are reported as a percentage of 82DI WT titer and represent the mean of 2 trials. Panel D is a photograph of a gel of HEK 293 cells transfected with helper and rep-cap plasmids as denoted above lane: (WT) WT AAP; (s60) AAPstop60; (s20) AAPstop20; (r) AAPstop20 plus CMV-driven AAP2. Whole cell lysates were harvested after 36 hours, and VP levels interrogated by Western Blot. Tubulin was used as a loading control. Panel E is normalized SYPRO® Orange fluorescence signals obtained for Anc82 and 82DI. Panel F are photographs of GFP fluorescence detected in murine livers 30 d after systemic injection with $1\times10^{11}$ vg/mouse of Anc82, 82DI, or AAV8. Each image is representative of an individual animal. See also FIGS. 12 and 13.

FIGS. 5A-F are a series of molecular-level and atomic-level schematics demonstrating that sites of interest map to the trimer interface, suggesting stronger inter-monomeric interactions in AAPC-independent serotypes. Panel A is a summary of the ten sites (twelve residues) identified by Branch D/Branch I multiple sequence alignment, numbered from VP1 start codon. Branch D residues include Anc80, Anc81, Anc82, Anc83, Anc84, AAV8, and rh10; Branch I residues include Anc110, rh8, and AAV9. Variations in identity for AAV8 and AAV9 are indicated in parentheses and are exclusive to these members of their respective branches. Panel B is a side view of an AAV9 trimer, showing planes of view in Panel C. Each monomer is represented as one color, and each site of interest in a darker shade of that color. Numbered arrows indicate each site within the red monomer. Panels D-F are atomic-level views of select sites in AAV8 and AAV9 trimers.

FIGS. 6A-C are a series of schematics and gels of experimental data demonstrating that AAP promotes VP-VP interactions. Panel A is a schematic of expression constructs for AAP2 and VP1 and VP3 of AAV2, AAV3, Anc82, and 82DI. In CMV-HA-VP1, the VP2 and VP3 start codons were modified to silence their expression, and the AAPstop60 mutation (red rectangle) was included. Panel B are photographs of HEK293 cells transfected with CMV-HA-VP1 and CMV-VP3 of serotype indicated above each lane, +/−CMV-AAP2, and lysates harvested after 48 h. Immunoprecipitation was performed using anti-HA antibody; VPs detected by Western Blot using the B1 antibody. Panel C are photographs of lysates from CMV-HA-VP1, CMV-VP3, +/−CMV-AAP2 (all AAV2 proteins) transfected HEK293 cells treated with DMSO, 5 mM disuccinimidyl glutarate (DSG), or 5 mM disuccinimidyl suberate (DSS) as indicated above columns. VPs were detected by Western Blot with B1 antibody. Approximate molecular weights are shown to the right of each row. See also FIG. 13.

FIGS. 10A-C are a series of schematics and graphs of experimental data demonstrating that AAV3 AAPN does not rescue AAP-dependent viral production. Related to FIGS. 3A-E. Panel A are constructs expressing only AAP generated by adding early stop codons in the VP1, VP2, and VP3 ORFs of an AAV3 genome, and the AAPstop60 mutation was included to generate a construct expressing only AAPN. The VP3 early stop codon is a silent mutation in the AAP ORF. Panel B is a graph from constructs in (A) used to trans-complement AAPstop20 viral production in AAV2 and AAV3 (green and red bars) and viral titers reported as a percentage of their WT titer. Graph represents average of two trials. † Titer below background (no cap gene control) in at least one trial. Panel C shows the individual data for both trials.

FIGS. 11A-D are a series of representations of microscope images and graphs that show experimental data demonstrating that AAPstop60 virus is indistinguishable from wt AAP virus. Related to FIGS. 1A-E. Panel A are photographs of AAV3 and AAV3AAPstop60.CMV.EGFP.T2A.Luciferase vector stained with uranyl acetate and imaged by TEM. Panels B and C are results from HEK293 cells incubated with hAd5 (MOI=20) overnight, then AAV3, AAV3AAPstop60, AAV9 or AAV9AAPstop60.CMV.EGFP.T2A.Luciferase was added at GC/well indicated on x-axis in Panel C. GFP fluorescence was imaged at 48 h (Panel B; images represent the highest titer for each vector). Luciferase activity was quantified at 48 h (Panel C). Panel D is normalized SYPRO® Orange fluorescence signals obtained for AAV3 and AAV9 WT and AAPstop60 vectors.

FIGS. 12A-B are a series of graphs that show experimental data of Anc82 vs Anc82DI in vitro and in vivo as follows. Related to FIGS. 4A-F. Panel A is a graph of HEK293 cells incubated with hAd5 (MOI=20) overnight, then Anc82 or Anc82DI.CMV.EGFP.T2A.Luciferase vector added at $1\times10^9$ or $1\times10^8$ GC/well as indicated. Luciferase activity was measured after 48 h. Panel B is a graph of mice injected systemically with $1\times10^{11}$ vg/mouse of Anc82, 82DI, or AAV8.CB7.CI.EGFP.FF2A.hA1AT.RBG. Human a-1 antitrypsin (hA1AT) levels were measured by ELISA in serum sampled on time points indicated on x axis.

FIGS. 13A-B are a pair of bar graphs of experimental data showing that the IP fraction does not contain fully assembled capsids. Related to FIG. 6. Rep, helper, and ITR-CMV-EGFP-T2A-Luc_ITR reporter genome plasmids were transfected with the AAV2 protein expression constructs indicated on x-axis. Fully assembled vectors in the input, IP, and supernatant fractions were quantified by (Panel A) qPCR on DNase resistant genomes or (Panel B) A20 capsid ELISA. Graphs are representative of two independent experiments. † At least one measurement falls below the limit of detection.

DETAILED DESCRIPTION

Figure 4F:
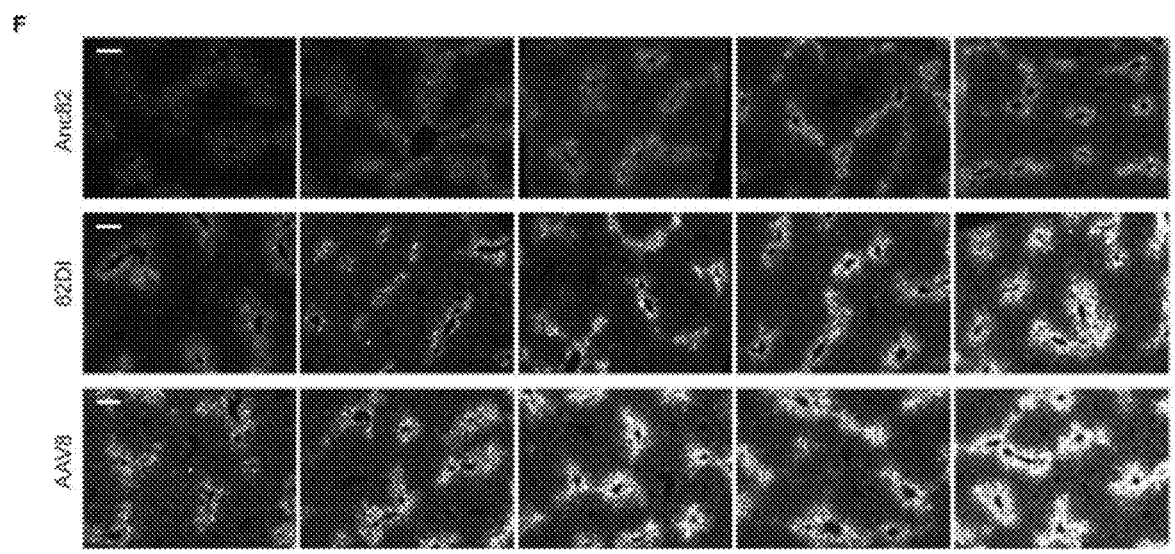
Figure 7:
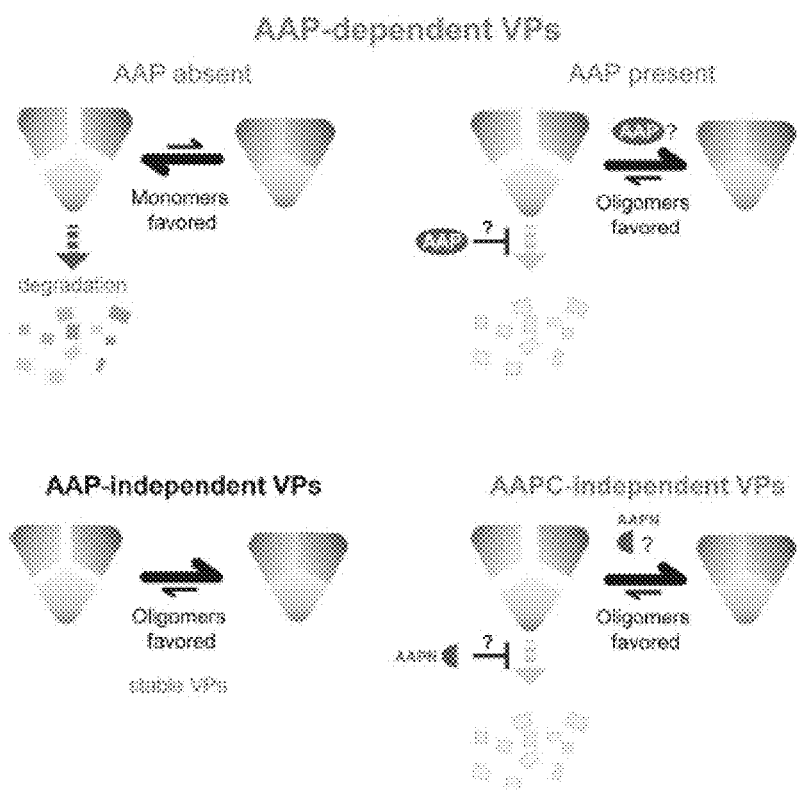
FIG. 7 is a schematic model for early steps of capsid assembly across the AAP phenotypes. Whether a serotype is AAP-dependent, AAP-independent, or AAPC-independent, nucleating capsid assembly is likely dependent on both the stability and oligomerization of VP proteins. The findings herein demonstrate AAP is active in both functions. Whether or not these functions are separate is unclear, and indicated by question marks in the model.

Gene transfer, either for experimental or therapeutic purposes, relies upon a vector or vector system to shuttle genetic information into target cells. The vector or vector system is considered the major determinant of efficiency, specificity, host response, pharmacology, and longevity of the gene transfer reaction. Currently, the most efficient and effective way to accomplish gene transfer is through the use of vectors or vector systems based on viruses that have been made replication-defective. One of the most common viruses to be made replication-defective and used in gene transfer is adeno-associated virus (AAV).

The AAV capsid is a non-enveloped, icosahedral 60-mer of three repeating protein monomer subunits called viral protein 1 (VP1), VP2, and VP3. A single transcript expressed from the AAV cap gene containing nested open reading frames (ORFs) is alternately spliced, resulting in three distinct protein products that share C-terminal identity the length of VP3. A 1:1:10 stoichiometry of VP1:VP2:VP3 in the assembled capsid is thought to be a consequence of the relative abundance of each protein, which is, in turn, regulated by splice product abundance and a non-canonical ACG translation start codon for VP2.

The Assembly-Activating Protein (AAP) is a non-structural protein expressed from a non-canonical CTG start codon of an overlapping reading frame embedded within the capsid (cap) gene of AAV. AAV serotypes have different requirements for AAP, with some AAV serotypes exhibiting AAP-dependence (e.g., AAV8, rh10, Anc80, Anc81, Anc82, Anc83, and Anc84) and other AAV serotypes exhibiting AAP-independence (e.g., AAV9, rh8, and Anc110).

As used herein, an ancestral scaffold sequence refers to a non-naturally occurring sequence that is constructed using evolutionary probabilities and evolutionary modeling and is not known to have ever existed or to presently exit in nature. These scaffold sequences were leveraged herein to interrogate AAP function and delineate structural determinants within the capsid relevant to the virus' requirement for AAP.

This disclosure provides methods of modifying the AAP-dependence of an AAV. For example, an AAV capsid sequence can be engineered to include the motif identified herein, which reduces the AAP-dependence (or, conversely, increases the AAP-independence) during packaging of the AAV. This provides a number of benefits during manufacturing including, without limitation, the ability to reduce the number of components needed for productive particle assembly in any AAV production system (e.g. mammalian, yeast, insect cell), the ability to optimize AAV capsid structure with reduced constraints imposed by AAP, the potential of AAV capsid self assembly from minimal components, and the reduction of AAP contamination concerns in the final vector preparations.

Adeno-Associated Virus (AAV) Nucleic Acid and Polypeptide Sequences Imparting Modified AAP-Dependency A non-naturally occurring AAV capsid sequence, based originally on the Anc82 sequence (SEQ ID NO: 1, encoded by SEQ ID NO:2, both shown below), which exhibits AAP-dependence during packaging, has been modified as described herein to produce Anc82DI (SEQ ID NO:3, encoded by SEQ ID NO:4, both shown below). Anc82DI exhibits AAP-independence during packaging, but appears to retain functionality as a potent gene transfer vector. The sequence motif that imparts AAP-independence on AAP-dependent sequences is provided in Table 1 above.

```
Anc82 protein (SEQ ID NO: 1)
MAADGYLPDWLEDNLSEGIREWWDLKPGAPKPKANQQKQDDGRGLVLPGYKYLGPFNGLDKGEPVNAADAAA

LEHDKAYDQQLKAGDNPYLRYNHADAEFQERLQEDTSFGGNLGRAVFQAKKRVLEPLGLVEEGAKTAPGKKR

PVEQSPQREPDSSTGIGKKGQQPAKKRLNFGQTGDSESVPDPQPLGEPPAAPSGVGSNTMAAGGGAPMADNN

EGADGVGNSSGNWHCDSTWLGDRVITTSTRTWALPTYNNHLYKQISNGTSGGSTNDNTYFGYSTPWGYFDFN

RFHCHFSPRDWQRLINNNWGFRPKRLNFKLFNIQVKEVTTNEGTKTIANNLTSTVQVFTDSEYQLPYVLGSA

HQGCLPPFPADVFMIPQYGYLTLNNGSQAVGRSSFYCLEYFPSQMLRTGNNFQFSYTFEDVPFHSSYAHSQS

LDRLMNPLIDQYLYYLSRTQTTGGTAGTQTLQFSQAGPSSMANQAKNWLPGPCYRQQRVSTTTNQNNNSNFA

WTGATKYHLNGRDSLVNPGVAMATHKDDEDRFFPSSGVLIFGKQGAGNDNVDYSNVMITSEEEIKTTNPVAT

EEYGVVATNLQSANTAPQTGTVNSQGALPGMVWQNRDVYLQGPIWAKIPHTDGNFHPSPLMGGFGLKHPPPQ

ILIKNTPVPADPPTTFNQAKLNSFITQYSTGQVSVEIEWELQKENSKRWNPEIQYTSNYYKSTNVDFAVNTE

GVYSEPRPIGTRYLTRNL
```

-continued

Anc82 DNA (SEQ ID NO: 2)
ATGGCTGCCGATGGTTATCTTCCAGATTGGCTCGAGGACAACCTCTCTGAGGGCATTCGCGAGTGGTGGGAC

CTGAAACCTGGAGCCCCGAAACCCAAAGCCAACCAGCAAAAGCAGGACGACGGCCGGGGTCTGGTGCTTCCT

GGCTACAAGTACCTCGGACCCTTCAACGGACTCGACAAGGGGGAGCCCGTCAACGCGGCGGACGCAGCGGCC

CTCGAGCACGACAAGGCCTACGACCAGCAGCTCAAAGCGGGTGACAATCCGTACCTGCGGTATAATCACGCC

GACGCCGAGTTTCAGGAGCGTCTGCAAGAAGATACGTCTTTTGGGGGCAACCTCGGGCGAGCAGTCTTCCAG

GCCAAGAAGCGGGTTCTCGAACCTCTCGGTCTGGTTGAGGAAGGCGCTAAGACGGCTCCTGGAAAGAAGAGG

CCGGTAGAGCAGTCACCACAGCGTGAGCCCGACTCCTCCACGGGCATCGGCAAGAAAGGCCAGCAGCCCGCC

AAAAAGAGACTCAATTTCGGTCAGACTGGCGACTCAGAGTCAGTCCCCGACCCTCAACCTCTCGGAGAACCT

CCAGCAGCGCCCTCTGGTGTGGGATCTAATACAATGGCTGCAGGCGGTGGCGCACCAATGGCAGACAATAAC

GAAGGTGCCGACGGAGTGGGTAATTCCTCGGGAAATTGGCATTGCGATTCCACATGGCTGGGCGACAGAGTC

ATCACCACCAGCACCCGAACCTGGGCCCTGCCCACCTACAACAACCACCTCTACAAGCAAATCTCCAACGGG

ACCTCGGGAGGCAGCACCAACGACAACACCTACTTTGGCTACAGCACCCCCTGGGGGTATTTTGACTTTAAC

AGATTCCACTGCCACTTCTCACCACGTGACTGGCAGCGACTCATCAACAACAACTGGGGATTCCGGCCCAAG

AGACTCAACTTCAAGCTCTTCAACATCCAGGTCAAAGAGGTCACGACGAATGAAGGCACCAAGACCATCGCC

AATAACCTCACCAGCACCGTCCAGGTGTTTACGGACTCGGAATACCAGCTGCCGTACGTCCTCGGCTCTGCC

CACCAGGGCTGCCTGCCTCCGTTCCCGGCGGACGTCTTCATGATTCCTCAGTACGGCTACCTGACTCTCAAC

AACGGTAGTCAGGCCGTGGGACGTTCCTCCTTCTACTGCCTGGAGTACTTCCCCTCTCAGATGCTGAGAACG

GGCAACAACTTTCAATTCAGCTACACTTTCGAGGACGTGCCTTTCCACAGCAGCTACGCGCACAGCCAGAGT

TTGGACAGGCTGATGAATCCTCTCATCGACCAGTACCTGTACTACCTGTCAAGAACCCAGACTACGGGAGGC

ACAGCGGGAACCCAGACGTTGCAGTTTTCTCAGGCCGGGCCTAGCAGCATGGCGAATCAGGCCAAAAACTGG

CTGCCTGGACCCTGCTACAGACAGCAGCGCGTCTCCACGACAACGAATCAAAACAACAACAGCAACTTTGCC

TGGACTGGTGCCACCAAGTATCATCTGAACGGCAGAGACTCTCTGGTGAATCCGGGCGTCGCCATGGCAACC

CACAAGGACGACGAGGACCGCTTCTTCCCATCCAGCGGCGTCCTCATATTTGGCAAGCAGGGAGCTGGAAAT

GACAACGTGGACTATAGCAACGTGATGATAACCAGCGAGGAAGAAATCAAGACCACCAACCCCGTGGCCACA

GAAGAGTATGGCGTGGTGGCTACTAACCTACAGTCGGCAAACACCGCTCCTCAAACGGGGACCGTCAACAGC

CAGGGAGCCTTACCTGGCATGGTCTGGCAGAACCGGGACGTGTACCTGCAGGGTCCTATTTGGGCCAAGATT

CCTCACACAGATGGCAACTTTCACCCGTCTCCTTTAATGGGCGGCTTTGGACTTAAACATCCGCCTCCTCAG

ATCCTCATCAAAAACACTCCTGTTCCTGCGGATCCTCCAACAACGTTCAACCAGGCCAAGCTGAATTCTTTC

ATCACGCAGTACAGCACCGGACAAGTCAGCGTGGAGATCGAGTGGGAGCTGCAGAAGGAGAACAGCAAGCGC

TGGAACCCAGAGATTCAGTATACTTCCAACTACTACAAATCTACAAATGTGGACTTTGCTGTTAATACTGAG

GGTGTTTACTCTGAGCCTCGCCCCATTGGCACTCGTTACCTCACCCGTAATCTGTAA

Anc82DI protein (SEQ ID NO: 3):
MAADGYLPDWLEDNLSEGIREWWDLKPGAPKPKANQQKQDDGRGLVLPGYKYLGPFNGLDKGEPVNAADAAA

LEHDKAYDQQLKAGDNPYLRYNHADAEFQERLQEDTSFGGNLGRAVFQAKKRVLEPLGLVEEGAKTAPGKKR

PVEQSPQREPDSSTGIGKSGQQPAKKRLNFGQTGDSESVPDPQPLGEPPAAPSGVGSNTMASGGGAPMADNN

EGADGVGNSSGNWHCDSTWLGDRVITTSTRTWALPTYNNHLYKQISNGTSGGSTNDNTYFGYSTPWGYFDFN

RFHCHFSPRDWQRLINNNWGFRPKRLNFKLFNIQVKEVTTNEGTKTIANNLTSTVQVFTDSEYQLPYVLGSA

HQGCLPPFPADVFMIPQYGYLTLNNGSQAVGRSSFYCLEYFPSQMLRTGNNFQFSYTFEDVPFHSSYAHSQS

LDRLMNPLIDQYLYYLSRTQTTGGTAGTQTLQFSQAGPSSMANQARNWVPGPCYRQQRVSTTTNQNNNSNFA

WTGATKYHLNGRDSLMNPGVAMASHKDDEDRFFPSSGVLIFGKQGAGNDNVDYSNVMITSEEEIKTTNPVAT

EEYGVVATNHQSANTQAQTGTVQNQGILPGMVWQNRDVYLQGPIWAKIPHTDGNFHPSPLMGGFGLKHPPPQ

-continued

ILIKNTPVPADPPTTFNQAKLNSFITQYSTGQVSVEIEWELQKENSKRWNPEIQYTSNYYKSTNVDFAVNTE

GVYSEPRPIGTRYLTRNL

Anc82DI DNA (SEQ ID NO: 4):
ATGGCTGCCGATGGTTATCTTCCAGATTGGCTCGAGGACAACCTCTCTGAGGGCATTCGCGAGTGGTGGGAC

CTGAAACCTGGAGCCCCGAAACCCAAAGCCAACCAGCAAAAGCAGGACGACGGCCGGGGTCTGGTGCTTCCT

GGCTACAAGTACCTCGGACCCTTCAACGGACTCGACAAGGGGGAGCCCGTCAACGCGGCGGACGCAGCGGCC

CTCGAGCACGACAAGGCCTACGACCAGCAGCTCAAAGCGGGTGACAATCCGTACCTGCGGTATAATCACGCC

GACGCCGAGTTTCAGGAGCGTCTGCAAGAAGATACGTCTTTTGGGGGCAACCTCGGGCGAGCAGTCTTCCAG

GCCAAGAAGCGGGTTCTCGAACCTCTCGGTCTGGTTGAGGAAGGCGCTAAGACGGCTCCTGGAAAGAAGAGG

CCGGTAGAGCAGTCACCACAGCGTGAGCCCGACTCCTCCACGGGCATCGGCAAGAGCGGCCAGCAGCCCGCC

AAAAAGAGACTCAATTTCGGTCAGACTGGCGACTCAGAGTCAGTCCCCGACCCTCAACCTCTCGGAGAACCT

CCAGCAGCGCCCTCTGGTGTGGGATCTAATACAATGGCTTCAGGCGGTGGCGCACCAATGGCAGACAATAAC

GAAGGTGCCGACGGAGTGGGTAATTCCTCGGGAAATTGGCATTGCGATTCCACATGGCTAGGCGACAGAGTC

ATCACCACCAGCACCCGAACCTGGGCCCTGCCCACCTACAACAACCACCTCTACAAGCAAATCTCCAACGGG

ACCTCGGGAGGCAGCACCAACGACAACACCTACTTTGGCTACAGCACCCCCTGGGGGTATTTTGACTTTAAC

AGATTCCACTGCCACTTCTCACCACGTGACTGGCAGCGACTCATCAACAACAACTGGGGATTCCGGCCCAAG

AGACTCAACTTCAAGCTCTTCAACATCCAGGTCAAAGAGGTCACGACGAATGAAGGCACCAAGACCATCGCC

AATAACCTCACCAGCACCGTCCAGGTGTTTACGGACTCGGAATACCAGCTGCCGTACGTCCTCGGCTCTGCC

CACCAGGGCTGCCTGCCTCCGTTCCCGGCGGACGTCTTCATGATTCCTCAGTACGGCTACCTGACTCTCAAC

AACGGTAGTCAGGCCGTGGGACGTTCCTCCTTCTACTGCCTGGAGTACTTCCCCTCTCAGATGCTGAGAACG

GGCAACAACTTTCAATTCAGCTACACTTTCGAGGACGTGCCTTTCCACAGCAGCTACGCGCACAGCCAGAGT

TTGGACAGGCTGATGAATCCTCTCATCGACCAGTACCTGTACTACCTGTCAAGAACCCAGACTACGGGAGGC

ACAGCGGGAACCCAGACGTTGCAGTTTTCTCAGGCCGGGCCTAGCAGCATGGCGAATCAGGCCAGAAACTGG

GTGCCTGGACCCTGCTACAGACAGCAGCGCGTCTCCACGACAACGAATCAAAACAACAACAGCAACTTTGCC

TGGACTGGTGCCACCAAGTATCATCTGAACGGCAGAGACTCTCTGATGAATCCGGGCGTCGCCATGGCAAGC

CACAAGGACGACGAGGACCGCTTCTTCCCATCCAGCGGCGTCCTCATATTTGGCAAGCAGGGAGCTGGAAAT

GACAACGTGGACTATAGCAACGTGATGATAACCAGCGAGGAAGAAATCAAGACCACCAACCCCGTGGCCACA

GAAGAGTATGGCGTGGTGGCTACTAACCACCAGTCGGCAAACACCCAGGCTCAAACGGGGACCGTCCAAAAC

CAGGGAATCTTACCTGGCATGGTCTGGCAGAACCGGGACGTGTACCTGCAGGGTCCTATTTGGGCCAAGATT

CCTCACACAGATGGCAACTTTCACCCGTCTCCTTTAATGGGCGGCTTTGGACTTAAACATCCGCCTCCTCAG

ATCCTCATCAAAAACACTCCTGTTCCTGCGGATCCTCCAACAACGTTCAACCAGGCCAAGCTGAATTCTTTC

ATCACGCAGTACAGCACCGGACAAGTCAGCGTGGAGATCGAGTGGGAGCTGCAGAAGGAGAACAGCAAGCGC

TGGAACCCAGAGATTCAGTATACTTCCAACTACTACAAATCTACAAATGTGGACTTTGCTGTTAATACTGAG

GGTGTTTACTCTGAGCCTCGCCCCATTGGCACTCGTTACCTCACCCGTAATCTGTAA

In addition to the polypeptides having the amino acid sequences shown in SEQ ID NOs: 1 and 3, polypeptides are provided that have at least 95% sequence identity (e.g., at least 96%, at least 97%, at least 98%, at least 99% or 100% sequence identity) to the 55 polypeptides having the amino acid sequences shown in SEQ ID NOs: 1 and 3.

Similarly, nucleic acid molecules are provided that have at least 95% sequence identity (e.g., at least 96%, at least 97%, at least 98%, at least 99% or 100% sequence identity) to the nucleic acid molecules shown in SEQ ID NOs: 2 and 4.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the algorithm described by Altschul et al. (1997, Nucleic Acids Res., 25:3389 3402) as incorporated into BLAST (basic local alignment search tool) programs, available at ncbi.nlm.nih.gov on the World Wide Web. BLAST searches can be performed to determine percent sequence identity between a sequence (nucleic acid or amino acid) and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence and another sequence, the default parameters of the respective programs generally are used.

This disclosure also provides vectors containing nucleic acid molecules that encode polypeptides. Vectors, including expression vectors, are commercially available or can be produced by recombinant technology. A vector containing a nucleic acid molecule can have one or more elements for expression operably linked to such a nucleic acid molecule, and further can include sequences such as those encoding a selectable marker (e.g., an antibiotic resistance gene), and/or those that can be used in purification of a polypeptide (e.g., 6×His tag). Elements for expression include nucleic acid sequences that direct and regulate expression of nucleic acid coding sequences. One example of an expression element is a promoter sequence. Expression elements also can include one or more of introns, enhancer sequences, response elements, or inducible elements that modulate expression of a nucleic acid molecule. Expression elements can be of bacterial, yeast, insect, mammalian, or viral origin and vectors can contain a combination of expression elements from different origins. As used herein, operably linked means that elements for expression are positioned in a vector relative to a coding sequence in such a way as to direct or regulate expression of the coding sequence.

A nucleic acid molecule, e.g., a nucleic acid molecule in a vector (e.g., an expression vector, such as a viral vector) can be introduced into a host cell. The term "host cell" refers not only to the particular cell(s) into which the nucleic acid molecule has been introduced, but also to the progeny or potential progeny of such a cell. Many suitable host cells are known to those skilled in the art; host cells can be prokaryotic cells (e.g., E. coli) or eukaryotic cells (e.g., yeast cells, insect cells, plant cells, mammalian cells). Representative host cells can include, without limitation, A549, WEHI, 3T3, 10T½, BHK, MDCK, COS 1, COS 7, BSC 1, BSC 40, BMT 10, VERO, WI38, HeLa, 293 cells, Saos, C2C12, L cells, HT1080, HepG2 and primary fibroblast, hepatocyte and myoblast cells derived from mammals including human, monkey, mouse, rat, rabbit, and hamster. Methods for introducing nucleic acid molecules into host cells are well known in the art and include, without limitation, calcium phosphate precipitation, electroporation, heat shock, lipofection, microinjection, and viral-mediated nucleic acid transfer (e.g., transduction).

With respect to polypeptides, "purified" refers to a polypeptide (i.e., a peptide or a polypeptide) that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is considered "purified," but further can be removed from the components used to synthesize the polypeptide (e.g., amino acid residues). With respect to nucleic acid molecules, "isolated" refers to a nucleic acid molecule that is separated from other nucleic acid molecules that are usually associated with it in the genome. In addition, an isolated nucleic acid molecule can include an engineered nucleic acid molecule such as a recombinant or a synthetic nucleic acid molecule.

Polypeptides can be obtained (e.g., purified) from natural sources (e.g., a biological sample) by known methods such as DEAE ion exchange, gel filtration, and/or hydroxyapatite chromatography. A purified polypeptide also can be obtained, for example, by expressing a nucleic acid molecule in an expression vector or by chemical synthesis. The extent of purity of a polypeptide can be measured using any appropriate method, e.g., column chromatography, polyacrylamide gel electrophoresis, or HPLC analysis. Similarly, nucleic acid molecules can be obtained (e.g., isolated) using routine methods such as, without limitation, recombinant nucleic acid technology (e.g., restriction enzyme digestion and ligation) or the polymerase chain reaction (PCR; see, for example, PCR Primer: A Laboratory Manual, Dieffenbach & Dveksler, Eds., Cold Spring Harbor Laboratory Press, 1995). In addition, isolated nucleic acid molecules can be chemically synthesized.

Methods of Making Virus Particles Having Modified AAP-Dependence

After the desired sequence of a virus or portion thereof has been determined (e.g., having a modified AAP-dependency), the actual nucleic acid molecule and/or polypeptide(s) can be generated, e.g., synthesized. Methods of generating an artificial nucleic acid molecule or polypeptide based on a sequence obtained, for example, in silico, are known in the art and include, for example, chemical synthesis or recombinant cloning. Additional methods for generating nucleic acid molecules or polypeptides are known in the art and are discussed in more detail below.

Once a polypeptide has been produced, or once a nucleic acid molecule has been generated and expressed to produce a polypeptide, the polypeptide can be assembled into a virus particle using, for example, a packaging host cell. The components of a virus particle (e.g., rep sequences, cap sequences, inverted terminal repeat (ITR) sequences) can be introduced, transiently or stably, into a packaging host cell using one or more vectors as described herein.

Virus particles can be purified using routine methods. As used herein, "purified" virus particles refer to virus particles that are removed from components in the mixture in which they were made such as, but not limited to, viral components (e.g., rep sequences, cap sequences), packaging host cells, and partially- or incompletely-assembled virus particles.

Once assembled, the virus particles can be screened for, e.g., the ability to replicate; gene transfer properties; receptor binding ability; and/or seroprevalence in a population (e.g., a human population). Determining whether a virus particle can replicate is routine in the art and typically includes infecting a host cell with an amount of virus particles and determining if the virus particles increase in number over time. Determining whether a virus particle is capable of performing gene transfer also is routine in the art and typically includes infecting host cells with virus particles containing a transgene (e.g., a detectable transgene such as a reporter gene, discussed in more detail below).

Following infection and clearance of the virus, the host cells can be evaluated for the presence or absence of the transgene. Determining whether a virus particle binds to its receptor is routine in the art, and such methods can be performed in vitro or in vivo.

Determining the seroprevalence of a virus particle is routinely performed in the art and typically includes using an immunoassay to determine the prevalence of one or more antibodies in samples (e.g., blood samples) from a particular population of individuals. Seroprevalence is understood in the art to refer to the proportion of subjects in a population that is seropositive (i.e., has been exposed to a particular pathogen or immunogen), and is calculated as the number of subjects in a population who produce an antibody against a particular pathogen or immunogen divided by the total number of individuals in the population examined. Immunoassays are well known in the art and include, without limitation, an immunodot, Western blot, enzyme immunoassays (EIA), enzyme-linked immunosorbent assay (ELISA), or radioimmunoassay (RIA). Simply by way of example, see Xu et al. (2007, Am. J. Obstet. Gynecol., 196:43.e1-6); Paul et al. (1994, J. Infect. Dis., 169:801-6); Sauerbrei et al. (2011, Eurosurv., 16(44):3); Boutin et al. (2010, Hum. Gene Ther., 21:704-12); Calcedo et al. (2009, J. Infect. Dis., 199:381-90); and Sakhria et al. (2013, PLoS Negl. Trop. Dis., 7:e2429), each of which determined seroprevalence for a particular antibody in a given population.

As described herein, virus particles can be neutralized by a person's, e.g., patient's, immune system. Several methods to determine the extent of neutralizing antibodies in a serum sample are available. For example, a neutralizing antibody assay measures the titer at which an experimental sample contains an antibody concentration that neutralizes infection by 50% or more as compared to a control sample without antibody. See, also, Fisher et al. (1997, Nature Med., 3:306-12) and Manning et al. (1998, Human Gene Ther., 9:477-85).

Methods of Using Viruses or Portions Thereof Having Modified AAP-Dependence

A virus or portion thereof that has a modified AAP-dependence as described herein can be used in a number of research and/or therapeutic applications. For example, a virus or portion thereof that has a modified AAP-dependence as described herein can be used in human or animal medicine for gene therapy (e.g., in a vector or vector system for gene transfer) or for vaccination (e.g., for antigen presentation). More specifically, a virus or portion thereof that has a modified AAP-dependence as described herein can be used for gene addition, gene augmentation, genetic delivery of a polypeptide therapeutic, genetic vaccination, gene silencing, genome editing, gene therapy, RNAi delivery, cDNA delivery, mRNA delivery, miRNA delivery, miRNA sponging, genetic immunization, optogenetic gene therapy, transgenesis, DNA vaccination, or DNA immunization.

A host cell can be transduced or infected with a virus or portion thereof having a modified AAP-dependence in vitro (e.g., growing in culture) or in vivo (e.g., in a subject). Host cells that can be transduced or infected with a virus or portion thereof having a modified AAP-dependence in vitro are described herein; host cells that can be transduced or infected with an ancestral virus or portion thereof in vivo include, without limitation, brain, liver, muscle, lung, eye (e.g., retina, retinal pigment epithelium), kidney, heart, gonads (e.g., testes, uterus, ovaries), skin, nasal passages, digestive system, pancreas, islet cells, neurons, lymphocytes, ear (e.g., inner ear), hair follicles, and/or glands (e.g., thyroid).

A virus or portion thereof having a modified AAP-dependence as described herein can be modified to include a transgene (in cis or trans with other viral sequences). A transgene can be, for example, a reporter gene (e.g., beta-lactamase, beta-galactosidase (LacZ), alkaline phosphatase, thymidine kinase, green fluorescent polypeptide (GFP), chloramphenicol acetyltransferase (CAT), or luciferase, or fusion polypeptides that include an antigen tag domain such as hemagglutinin or Myc) or a therapeutic gene (e.g., genes encoding hormones or receptors thereof, growth factors or receptors thereof, differentiation factors or receptors thereof, immune system regulators (e.g., cytokines and interleukins) or receptors thereof, enzymes, RNAs (e.g., inhibitory RNAs or catalytic RNAs), or target antigens (e.g., oncogenic antigens, autoimmune antigens)).

The particular transgene will depend, at least in part, on the particular disease or deficiency being treated. Simply by way of example, gene transfer or gene therapy can be applied to the treatment of hemophilia, retinitis pigmentosa, cystic fibrosis, leber congenital amaurosis, lysosomal storage disorders, inborn errors of metabolism (e.g., inborn errors of amino acid metabolism including phenylketonuria, inborn errors of organic acid metabolism including propionic academia, inborn errors of fatty acid metabolism including medium-chain acyl-CoA dehydrogenase deficiency (MCAD)), cancer, achromatopsia, cone-rod dystrophies, macular degenerations (e.g., age-related macular degeneration), lipopolypeptide lipase deficiency, familial hypercholesterolemia, spinal muscular atrophy, Duchenne's muscular dystrophy, Alzheimer's disease, Parkinson's disease, obesity, inflammatory bowel disorder, diabetes, congestive heart failure, hypercholesterolemia, hearing loss, coronary heart disease, familial renal amyloidosis, Marfan's syndrome, fatal familial insomnia, Creutzfeldt-Jakob disease, sickle-cell disease, Huntington's disease, fronto-temporal lobar degeneration, Usher syndrome, lactose intolerance, lipid storage disorders (e.g., Niemann-Pick disease, type C), Batten disease, choroideremia, glycogen storage disease type II (Pompe disease), ataxia telangiectasia (Louis-Bar syndrome), congenital hypothyroidism, severe combined immunodeficiency (SCID), and/or amyotrophic lateral sclerosis (ALS).

A transgene also can be, for example, an immunogen that is useful for immunizing a subject (e.g., a human, an animal (e.g., a companion animal, a farm animal, an endangered animal). For example, immunogens can be obtained from an organism (e.g., a pathogenic organism) or an immunogenic portion or component thereof (e.g., a toxin polypeptide or a by-product thereof). By way of example, pathogenic organisms from which immunogenic polypeptides can be obtained include viruses (e.g., picornavirus, enteroviruses, orthomyxovirus, reovirus, retrovirus), prokaryotes (e.g., Pneumococci, Staphylococci, *Listeria, Pseudomonas*), and eukaryotes (e.g., amebiasis, malaria, leishmaniasis, nematodes). It would be understood that the methods described herein and compositions produced by such methods are not to be limited by any particular transgene.

A virus or portion thereof having a modified AAP-dependence, usually suspended in a physiologically compatible carrier, can be administered to a subject (e.g., a human or non-human mammal). Suitable carriers include saline, which may be formulated with a variety of buffering solutions (e.g., phosphate buffered saline), lactose, sucrose, calcium phosphate, gelatin, dextran, agar, pectin, and water. The virus or portion thereof having a modified AAP-dependence is administered in sufficient amounts to transduce or infect the cells and to provide sufficient levels of gene transfer and expression to provide a therapeutic benefit without undue adverse effects. Conventional and pharmaceutically acceptable routes of administration include, but are not limited to, direct delivery to an organ such as, for example, the liver or lung, orally, intranasally, intratracheally, by inhalation, intravenously, intramuscularly, intraocularly, subcutaneously, intradermally, transmucosally, or by other routes of administration. Routes of administration can be combined, if desired.

The dose of the virus or portion thereof having a modified AAP-dependence that is administered to a subject will depend primarily on factors such as the condition being treated, and the age, weight, and health of the subject. For example, a therapeutically effective dosage of a virus or portion thereof having a modified AAP-dependence that is to be administered to a human subject generally is in the range of from about 0.1 ml to about 10 ml of a solution containing concentrations of from about $1\times10^1$ to $1\times10^{12}$ genome copies (GCs) of viruses (e.g., about $1\times10^3$ to $1\times10^9$ GCs). Transduction and/or expression of a transgene can be monitored at various time points following administration by DNA, RNA, or protein assays. In some instances, the levels of expression of the transgene can be monitored to determine the frequency and/or amount of dosage. Dosage regimens similar to those described for therapeutic purposes also may be utilized for immunization.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Vectors and Sequences

Adeno-associated viral vectors were pseudotyped with either extant or ancestral viral capsids. Extant capsids include AAV1 (Genbank [GB] AAD27757.1), AAV2 (GB AAC03780.1), AAV3 (GB U48704.1), AAV4 (GB U89790.1), AAV5 (GB AAD13756.1), AAV6 (GB AF028704.1), AAV7 (NC_006260.1) Rh.10 (gb AA088201.1), AAV8 (GB AAN03857.1), AAV9 (GB AAS99264.1), and Rh32.33 (GB EU368926). Ancestral AAV capsids include Anc80L65, Anc81, Anc82, Anc83, Anc84, Anc110, Anc113, Anc126, and Anc127 (KT235804-KT235812). In this study, Anc83 has the following mutation in the presumed AAP ORF: Q1L (83AAP-KI).

Example 2—Site Directed Mutagenesis

AAPstop60, AAPstop20, and 82DI single revertant mutations were generated using the QuikChange® II Site-Directed Mutagenesis Kit according to the manufacturer's instructions. To generate 82DI, the QuikChange® Lightning Multi Site-Directed Mutagenesis Kit was used according to the manufacturer's instructions, in two phases: first, five sites were mutated on an Anc82 backbone, then the remaining five mutations were introduced into this quintuple mutant backbone.

Example 3—Crude Virus Preparations/Titration

Virus preparations to assay production in all serotypes and mutants were prepared as follows: Polyethylenimine transfections of AAV cis ITR-CMV-EGFP-T2A-Luc-ITR (2 µg), AAV trans rep-cap (2 µg), and adenovirus helper plasmid (4 µg) were performed on HEK 293 cells at 90% confluency in 6-well dishes. PEI Max (Polysciences)/DNA ratio was maintained at 1.375:1 (w/w) in serum-free media. Virus was harvested after 72 h by three freeze/thaw cycles followed by centrifugation at 15000×g.

For DRP titers, crude preps were DNaseI treated, and resistant (packaged) vector genome copies were used to titrate preps by TaqMan qPCR amplification (Applied Biosystems 7500, Life Technologies) with primers and probes detecting CMV promoter regions of the transgene cassette.

Example 4—Thermostability Assay (AAV-ID)

Thermostability of purified vector was assayed by AAV-ID (Pacouret et al., 2017, Mol. Ther., 25:1375-86). Briefly, A 500 uL sample of SYPRO® Orange 50X was prepared using $PBS^{2+}$ (21-030-CV, Corning Inc., Corning, N.Y.) as a solvent. 96-well plates were loaded with 45 uL samples, supplemented with 5 uL Sypro Orange 50X. $PBS^{2+}$ and 0.25 mg/mL Lysozyme (L6876, SIGMA-ALDRICH, St. Louis, Mo., USA) solutions were used as negative and positive controls, respectively. Plates were sealed and centrifuged at 3000 rpm for 2 min, and subsequently loaded into a 7500 Real-Time PCR System (ThermoFisher SCIENTIFIC). Samples were incubated at 25° C. for 2 min prior to undergo a temperature gradient (25 to 99° C., ~2° C./10 min, step and hold mode with 0.4° C. temperature increments), while monitoring the fluorescence of the SYPRO® Orange dye using the ROX filter cube available on both qPCR systems. Fluorescence signals F were normalized between 0 and 100% and melting temperatures were defined as the temperature for which the numerical derivative dF/dT reached its maximum.

Example 5—Enzyme-Linked Immunosorbent Assays

A20 capsid ELISAs were performed on crude virus preparations with the PROGEN AAV 2 Titration ELISA kit (ref# PRATV), according to the manufacturer's instructions.

hA1AT ELISAs were performed on 1:1250-1:10000 serial dilutions of mouse serum with the Cloud-Clone ELISA kit for a-1 antitrypsin (SEB697Hu, 96 tests) according to the manufacturer's instructions.

Example 6—Animal Studies

C57BL/6 male mice (6-8 weeks) were purchased from Jackson Laboratories. All experimental procedures were performed in accordance with protocols approved by the Institutional Animal Care and Use Committee (IACUC) at Schepens Eye Research Institute.

Mice were anesthetized with Ketamine/Xylazine intraperitoneally. Each animal was injected retro-orbitally (100 µl) with 1.00E+11 VG/mouse of the following vectors: Anc82.CB7.CI.EGFP.FF2A.hA1AT.RBG and Anc82DI.CB7.CI.EGFP.FF2A.hA1AT.RBG. Blood was collected via submandibular bleeds using GoldenRod animal lancets (MEDIpoint, Inc.) prior injection, and 3, 7, 15 and 28 days post injection. Samples were centrifuged at 8,000 rpm for 7.5 minutes and the serum was collected.

Animals were euthanized, and livers were collected and submerged in 4% paraformaldehyde solution (Electron Microscopy Sciences) for 30 minutes, then placed in 30% sucrose overnight. The next day the liver was mounted in Tissue-Tek O.C.T. Compound (Sakura Finetek) and flash frozen in cool isopentane.

Example 7—Tissue Histology

To visualize eGFP expression in liver, 15 μm sections were mounted with VECTASHIELD® Hard Set™ mounting medium with DAPI (H-1500) and imaged with a Zeiss Axio Imager M2, at same gain and intensity across all sections.

Example 8—Molecular Representations

All molecular representations in this study were generated using PyMOL and Protein Data Bank files 2QA0 (AAV8) and 3UX1 (AAV9).

Example 9—Production and Purification of AAV3, AAV3s, AAV9 and AAV9s

Vectors were purified by affinity chromatography using either AVB Sepharose HP (25-4112-11, GE Healthcare) (AAV3 and AAV3s) or POROS CaptureSelect AAV9 affinity resin (Thermo Fisher) per the manufacturer instructions (AAV9 and AAV9s).

Large scale crude preps were treated with benzonase (250 U/mL, 1 h, 37° C.) before the centrifugation step (1 h, 10,000 rpm, 20° C.), then filtered using a 0.2 m Nalgene Rapid-Flow filter. Vectors were purified by affinity chromatography using either HiTrap columns prepacked with 1 mL AVB Sepharose HP (25-4112-11, GE Healthcare) (AAV3 and AAV3s) or a 5×125 mm Econoline column (TAC05/125PEO-AB-3, essentialLife Solutions) packed with 1 mL POROS CaptureSelect AAV9 affinity resin (Thermo Fisher) per the manufacturer instructions (AAV9 and AAV9s). Columns were sanitized with 5 column volumes (CV) 0.1 M $H_3PO_4$, 1 M NaCl, pH 2 (1 mL/min) and equilibrated with 5 CV PBS (21-030-CV, Corning) (1 mL/min). Clarified lysates were injected at 1 mL/min.

Columns were further washed with 10 CV PBS (1 mL/min). Vector particles were eluted in 3 mL 0.1 M NaOAc, 0.5 M NaCl, pH 2.5 (1 mL/min) and immediately neutralized with 400 μL of 1 M Tris-HCl, pH 10. Samples were further buffer-exchanged in PBS and concentrated by Amicon filtration (UFC910024, EMD Millipore) per the manufacturer instructions. Sample purity was assessed by SDS-PAGE, whereas DNAse I-resistant vector genomes were quantified by quantitative polymerase chain reaction (qPCR) using the TaqMan (Life Technologies) system with primers and probes targeting SV40 or eGFP.

Example 10—Statistical Methods

All data were analyzed using R prior to normalization for reporting in the figures (unless otherwise indicated). P-values are reported in Table 2, below. Viral titers were compared using a paired, one-tailed Student's t test and RNA levels were compared using a paired, two-tailed Student's t test.

TABLE 2

A

| FIG. 1C | Serotype | rh32.33 | AAV3 | AAV9 | AAV5 | AAV1 | AAV4 | rh8 | AAV6 | AAV2 | AAV7 | rh10 | AAV8 |
|---|---|---|---|---|---|---|---|---|---|---|---|---|---|
| | p-value | 0.013 | 0.038 | 0.033 | 0.090 | 0.075 | 0.114 | 0.004 | ND | ND | 0.002 | 0.017 | ND |
| FIG. 3A | Serotype | Anc113 | Anc110 | Anc126 | Anc127 | Anc81 | Anc84 | Anc82 | Anc83 | Anc80 | | | |
| | p-value | 0.918 | 0.003 | 0.079 | 0.048 | ND | ND | ND | ND | ND | | | |

| FIG. 4B | Serotype | Anc82 | Anc82 AAPs60 | 82DI AAPs60 |
|---|---|---|---|---|
| | Anc82 | — | ND | 0.03 |
| | 82DI | 0.94 | ND | 0.029 |

B

| | | minor | major | unspliced |
|---|---|---|---|---|
| FIG. 2C | WT/AAPstop60 | 0.581 | 0.299 | 0.075 |
| | WT/rescue | 0.354 | 0.185 | 0.111 |

Table 2 shows the statistical analysis related to FIGS. 1A-D, 2A-E, 3A-E, and 4A-F. See Table 3, below, for individual data of the titration by ELISA and qPCR for these figures. All statistical analysis was performed in R, on data prior to normalization for reporting in the main figures indicated at left of table. Panel A compares WT and AAPstop60 viral titers measured by qPCR after background subtraction (no cap gene control). P-values resulting from a paired, one-tailed t-test. ND="not determined"; a t-test could not be performed on serotypes with one or more trials within 3 standard deviations of measured background. Panel B compares AAPstop60 or rescue to WT levels of RNA (all normalized to GAPDH). P-values resulting from a paired, two-tailed t-test.

blots, and denatured in 4× NuPAGE® LDS sample buffer+ 0.5% βME at 90° C. 100 µg (FIGS. 2A-E) or 50 µg (FIGS. 3A-E and 4A-F) total protein (or dilution thereof for loading control blot) per well were loaded and electrophoresed on NuPAGE® 4-12% Bis-Tris gels.

For proteasome and lysosome inhibition experiments, media was removed 24 h after transfection and replaced with media containing the appropriate concentration of Bortezomib (Selleckchem PS-341), MLN7243 (Chemgood C-1233), Bafilomycin (Enzo BML-CM110-0100), or DMSO (for wt and AAPstop untreated samples) and incubated an additional 8 h. 25 µg total protein were loaded per well (diluted 1:10 for loading control). For protein turnover experiments by blocking protein synthesis, media was removed 24 h after transfection and replaced with media containing 50 µg/mL CHX (Sigma C7698) and lysates were harvested as described above at 1, 2, 4, 6, and 8 h time points, and for the 0 h time point media was not replaced but lysates were harvested. 10% FBS was maintained throughout all transfections and drug incubations described here.

TABLE 3

|  |  |  | AAV2 | | AAV3 | |
|---|---|---|---|---|---|---|
|  |  |  | WT | AAPstop60 | WT | AAPstop60 |
| Trial 1 | GC/mL: | qPCR | 1.34E+10 | 2.64E+07 | 1.72E+10 | 2.89E+09 |
|  | particles/mL: | ELISA | 2.48E+11 | 2.95E+08 | 6.14E+11 | 1.37E+11 |
|  | % WT: | qPCR | 100 | 0.197 | 100 | 16.813 |
|  |  | ELISA | 100 | 0.119 | 100 | 22.298 |
| Trial 2 | GC/mL: | qPCR | 8.25E+10 | 2.09E+08 | 1.76E+11 | 3.88E+10 |
|  | particles/mL: | ELISA | 6.78E+12 | 1.29E+09 | 2.23E+13 | 3.63E+12 |
|  | % WT: | qPCR | 100 | 0.253 | 100 | 22.045 |
|  |  | ELISA | 100 | 0.019 | 100 | 16.278 |
|  |  |  | AAV2 | | AAV3 | |
| Average % wt: |  | qPCR | 100 | 0.225 | 100 | 19.43 |
|  |  | ELISA | 100 | 0.069 | 100 | 19.29 |

Example 11—Expression Constructs

AAP-HA: Complimentary oligonucleotides encoding the Hemagglutinin (HA) tag with BsiWI overhangs (5' GTAC, 3' CATG) were annealed in T4 Ligase Buffer ramping from 95° C. to 25° C. at 5°/min, PNK treated, and ligated into BsiWI digested and CIP treated AAV1 and AAV3 wt and AAPstop60 rep-cap plasmids.

CMV-HA-VP1 and CMV-VP3: gBlocks® Gene Fragments (IDT) of bp #4-696 of VP1 for AAV2, AAV3, Anc82, and 82DI were obtained, with the following modifications: an EcoRI site, start codon, and HA sequence added to 5' end, ACG to ACC mutation of VP2 start codon, and ATG to CTG mutation of VP3 start codon. The gBlocks® include a BsrDI restriction site conserved in cap; gBlocks were digested with EcoRI and BsrDI. VP3 sequences were PCR amplified from the appropriate AAPstop60 rep-cap plasmids with primers incorporating 5' EcoRI and 3' HindIII restriction sites, then digested with either EcoRI and HindIII (for CMV-VP3) or BsrDI and HindIII (For CMV-HA-VP1). Fragments were ligated into pCDNA3.1(−) in the appropriate combinations. For CMV-AAP2, AAP was amplified from AAV2 rep-cap plasmid and ligated into pCDNA3.1(−).

Example 12—Protein Lysate Preparation and Degradation/Turnover Studies

Transfections were performed as in Crude Virus Preparation. At 36 h, supernatant was aspirated and cells lysed on plate with 100 µL (FIGS. 2A-E) or 150 µL (FIGS. 3A-E and 4A-F) lysis buffer (1% Triton X-100, 150 mM NaCl, 50 mM Tris, pH8, plus cOmplete Mini™ protease inhibitor). Lysate was clarified by centrifugation at 15,000×g, diluted 1:50 in lysis buffer for actin or 1:100 for tubulin loading control

Example 13—Western/Dot Blotting

Electrophoresed proteins were transferred to PVDF membranes, incubated with primary antibody (B1, 1:250, ARP#03-65158; Actin, 1:20000, Abcam 8227; Tubulin, 1:20000, Abcam 7291; HA, 1:5000, Abcam 9110; p62, 1:1000, Cell Signalling 5114) overnight, and detected with Anti-mouse (GE Healthcare LNXA931/AE) or Anti-rabbit (Sigma A0545) HRP conjugated secondary antibody and Thermo Super Signal® West Pico or Femto.

For dot blots, protein lysates were diluted 1:100 and 2 µL was spotted onto nitrocellulose membranes, allowed to dry, blocked in 5% milk, and incubated with ADK8 (ARP#03-651160) overnight.

Example 14—Immunoprecipitations

PEI transfections were performed with 10 µg each of CMV-HA-VP1, CMV-VP3, and CMV-AAP2 plasmid of the appropriate serotype (CMV-AAP2 added only where indicated) on 10 cm dishes of HEK 293 cells at ~80% confluency. PEI Max (Polysciences)/DNA ratio was maintained at 1.375:1 (w/w) in serum-free media. At 24 hours post transfection, cells were pelleted and resuspended in 1 mL lysis buffer (1% Triton X-100, 150 mM NaCl, 50 mM Tris, pH8, plus cOmplete Mini™ protease inhibitor). Immunoprecipitation was performed with rb Anti-HA antibody (Abcam 9110) and Pierce Protein A/G Plus Agarose beads. Precipitated proteins were eluted in 4× NuPAGE® LDS sample buffer+0.5% βME at 90° C. for 10 minutes. 10 μL (IP) or 30 μL (input) were loaded and electrophoresed on NuPAGE® 4-12% Bis-Tris gels and detected in Western Blotting above.

For detection of full virions (FIG. 6C), ITR-CMV-EGFP-T2A-Luc-ITR and pRep plasmids were added to the above transfection with AAV2. To avoid heat-denaturation of AAV2 capsids, complexes were instead eluted with 0.2 M glycine, pH 2.8, and eluates neutralized with equal volume Tris pH 8.5. Purified AAV2 preps were treated in parallel with elution and neutralization buffers to ensure these conditions did not denature the capsids. Control, IP, input, and supernatant fractions were DNaseI treated, and resistant (packaged) vector genome copies were quantified by TaqMan qPCR amplification (Applied Biosystems 7500, Life Technologies) with primers and probes detecting CMV promoter regions of the transgene cassette.

Example 15—Crosslinking

PEI transfections were performed with 2 μg each of CMV-HA-VP1, CMV-VP3, and CMV-AAP2 plasmid of the appropriate serotype (CMV-AAP2 added only where indicated) on 6-well plates of HEK 293 cells at ~80% confluency. PEI Max (Polysciences)/DNA ratio was maintained at 1.375:1 (w/w) in serum-free media. After 36 h, on-plate lysis was performed with M-PER™ (Thermo) buffer supplemented with cOmplete™ mini protease inhibitor. Lysate was divided into three and treated with 5 mM final concentration of disuccinimidyl glutarate (DSG, Thermo), disuccinimidyl suberate (DSS, Thermo), or an equal volume of DMSO as a mock treatment. Reactions were incubated on ice for 1 h, mixing periodically, then quenched with 1 M Tris. NuPAGE® LDS Sample Buffer+2-Mercaptoethanol were added and samples boiled for 10 minutes, loaded onto SDS-PAGE gel, and interrogated by Western Blot with B1 antibody.

Example 16—RNA Quantification

Transfections were performed as described in Crude Virus Preparations/Titration. RNA was harvested after 36 h with Qiagen RNeasy Mini® kit according to the manufacturer's instructions. TURBO DNA-free™ kit (Invitrogen) was used according to manufacturer's instructions (Rigorous DNase treatment protocol) to eliminate contaminating DNA from samples. cDNA synthesis was performed with iScript™ kit (BioRad) using 250 ng total RNA from each sample. Reactions were then diluted 10-fold, and 5 μL of diluted cDNA used in each qPCR reaction, prepared with PowerUp™ SYBR™ Green Master Mix (Applied Biosystems) and intron, intron-spanning, or GAPDH primers to detect unspliced, spliced, or housekeeping gene products.

Example 17—Transmission Electron Microscopy

For negative staining on chromatography-purified AAV3 and AAV3stop, vector samples (5 μL or 50 μL drop) and a blank buffer control were adsorbed onto 200 mesh carbon and formvar coated nickel grids, rinsed, and stained with 2% aqueous uranyl acetate for 30 seconds then absorbed off on filter paper and air dried. All grids were imaged using a FEI Tecnai G2 Spirit transmission electron microscope (FEI, Hillsboro, Oreg.) at 100 kV accelerating voltage, interfaced with an AMT XR41 digital CCD camera (Advanced Microscopy Techniques, Woburn, Mass.) for digital TIFF file image acquisition. TEM imaging of AAV samples were assessed and digital images captured at 2k×2k pixel, 16-bit resolution.

Example 18—In Vitro Transduction

The appropriate serotype and GC particles of AAV-CMV-EGFP-T2A-Luc was added to HEK-293 cells on a 96-well plate pre-infected with human adenovirus 5 (hAd5) 24 h prior at a multiplicity of infection of 20 particles/cell. The cells were imaged with an EVOS® FL Imaging System at 24 and 48 h, after which D-luciferin containing buffer was added and luminescence was measured using Synergy H1 microplate reader (BioTek; Winooski, Vt.).

Example 19—Requirement for AAP Ranges Broadly Across all AAV Clades

To test whether AAP is required to assemble capsids from the full complement of VP proteins (i.e., VP1, 2, and 3), AAP expression was abolished from rep-cap trans plasmids by an early stop codon in the AAP reading frame, a silent mutation in VP (FIG. 1A, AAPstop60). AAPstop60s were generated for 12 serotypes, including at least one member of each AAV clade, with the aim of a comprehensive assessment of AAP requirement across mammalian AAV serotypes. Considering AAP's non-canonical CTG start codon, AAPstop60 mutations were positioned such that they would be sufficiently downstream of potential alternate start codons, yet upstream of regions shown to be essential for AAP2 function (Naumer et al., 2012, J. Virol., 86:13038-48). To verify loss of AAP protein, a Hemagglutinin tag was inserted in the C-terminal region of the AAP ORF in two representative serotypes (FIG. 1A, AAP-HA). Whole cell lysates transfected with these constructs were analyzed by Western Blot (FIG. 1B), confirming that AAPstop60 results in loss of full-length AAP or any shorter protein product translated from alternate starts. A double band in the AAP-HA lane supports the likelihood of additional downstream start codons and corroborates the late placement of the stop codons (FIG. 1B).

Recombinant AAV vectors were produced from AAPstop60 and wildtype AAP (WT) plasmids, and titrated by qPCR quantifying DNase resistant particles (DRP). AAPstop60 vector titers reveal that when all three VP proteins are present, AAP is not strictly required to assemble the virion in several serotypes (FIG. 1C). Rather, AAP requirement ranges broadly across serotypes, with AAPstop60 vectors producing as high as 39% of WT titer for rh32.33, and as low as 0.035% WT titer for AAV8. This observation is in contrast with previous findings demonstrating AAP's absolute requirement for assembling VP3-only capsids, in particular AAV9 and AAV1 (Sonntag et al., 2011, J. Virol., 85:12686-97).

The advantage of DRP titration is the ability to quantify virus of any capsid serotype with the same vector genome absent of differential bias in measurement. However, DRP measures the amount of assembled particles that also underwent viral genome packaging, a process that occurs downstream of capsid assembly. Moreover, DRP does not assess for non-packaged, empty AAV virions. To directly assay capsid assembly and rule out the possibility that serotypes with low AAPstop60 titers were due to a packaging defect, an A20 capsid ELISA was performed, which recognizes a conformational epitope only present in assembled AAV2 capsids. A20 cross-reacts with AAV3, allowing us to assay assembly directly for an AAV that requires AAP (AAV2) and one that accomplishes assembly in the AAPstop60 context (AAV3). A20 ELISA data for both serotypes corroborated the DRP indirect measure of assembly (FIG. 1D).

Example 20—A Role for AAP in VP Protein Stability

To ensure that the observed range of AAP dependence for assembly was not due to variation in VP translation efficiencies imposed by alternate codon usage in the AAPstop60 mutants, VP protein levels produced by WT and AAPstop60 constructs were interrogated. The B1 monoclonal antibody detects a conserved linear epitope on VP proteins in denaturing conditions across all AAVs tested in this study except AAV4 and rh32.33, allowing nearly all serotypes to be assayed. No appreciable difference in VP2 or VP3 protein levels, and a slight decrease in VP1 levels, was observed for AAPstop60s that produce 10% or higher of their respective WT titers (FIG. 2A), whereas AAPstop60s with titers below this threshold show a dramatic decrease in VP protein levels (FIG. 2B).

To examine whether the observed decreases in VP levels were due to a potential translational defect, AAP2 was co-expressed in trans with AAPstop60 (rescue; FIG. 2B). Appreciable restoration of VP protein was observed for all affected serotypes. Furthermore, no difference was observed between WT, AAPstop60, or rescue transcript levels (FIG. 2C), indicating that VP protein loss in the absence of AAP most likely occurs post- (or co-) translationally.

To interrogate degradation as the mechanism for instability, AAV8 AAPstop60 transfected cells were treated with increasing concentrations of the proteasome inhibitor Bortezomib, the E1 inhibitor MLN7243, or the vacuolar specific H+ATPase inhibitor Bafilomycin (FIG. 2D). This allowed the examination of the earliest and latest steps of the Ubiquitin-Proteasome Pathway, as well as late steps of lysosomal degradation or autophagy by inhibiting the required acidification. Inhibiting lysosomal acidification resulted in a mild yet dose-dependent rescue of AAV8 VP3 protein. Proteasomal inhibition is accompanied by a robust rescue in AAV8 VP proteins in a dose dependent manner, but this was not concomitant with rescue of assembled capsids (FIG. 2E). E1 inhibition provided an equally mild to moderate VP rescue independent of drug concentration. Collectively, these results suggest that instability of VP proteins in the absence of AAP can primarily be attributed to proteasomal degradation, and that this may in part be Ubiquitin-independent. Lysosomal or autophagosomal degradation may also degrade a proportion of VP proteins.

Figure 8:
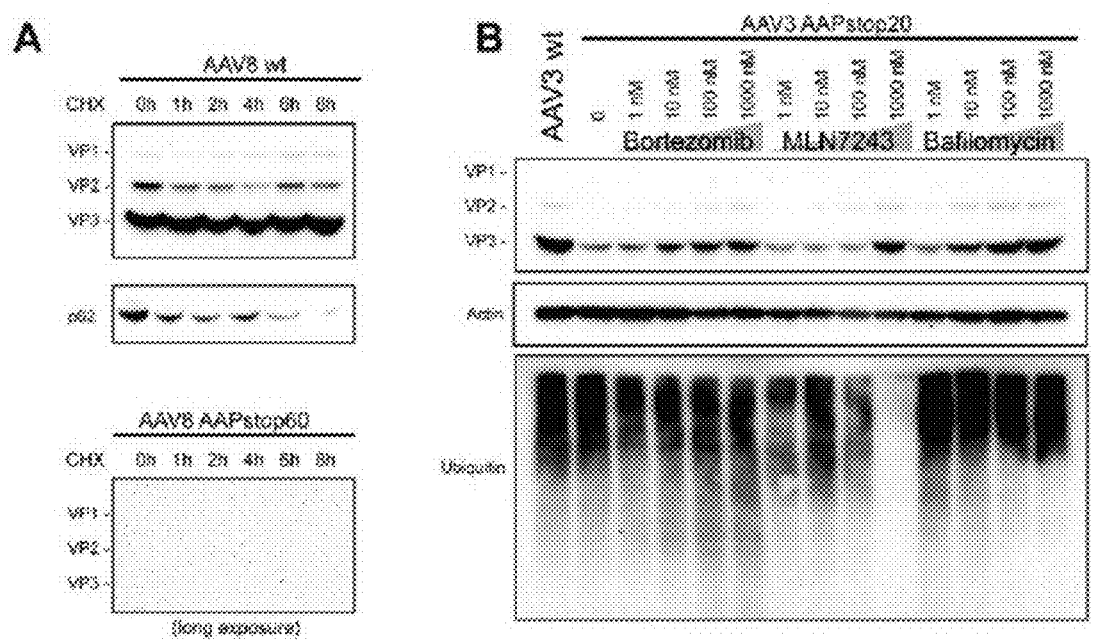
FIGS. 8A-B are a series of representations of gels showing AAV8 and AAV3 VP degradation. Related to FIGS. 2A-E and FIGS. 3A-E. Panel A are photographs of HEK 293 cells transfected with helper and AAV8 wt or AAPstop60 rep-cap plasmids as indicated. At 24 h, AAPstop60 transfected cells were treated with 50 µM cycloheximide (CHX) and lysates harvested at progressive time points. VP levels were interrogated by Western Blot with B1 antibody, and p62 was blotted for as a positive control for CHX effectiveness. The exposure shown for AAV8AAPstop60 transfected cells is a long exposure with a higher sensitivity detection reagent, to demonstrate that AAV8 VPs could not be detected in the absence of AAP. Panel B are photographs of HEK 293 cells transfected with helper and AAV3 wt or AAPstop20 rep-cap plasmids as indicated. At 24 h, AAPstop20 transfected cells were treated with concentrations of Bortezomib, MLN7243, or Bafilomycin as indicated above lanes, and incubated an additional 8 h before whole cell lysates were harvested. VP levels were interrogated by Western Blot with B1 antibody (top). Blot was stripped and reprobed for Ubiquitin (bottom). Actin was used as a loading control (middle).

In an attempt to examine the rate of AAV8 VP degradation, protein synthesis was blocked with Cycloheximide (CHX) and protein lysates were harvested at progressive time points (FIG. 8A). As expected in AAPstop60 lysates, VP protein levels were too low to detect even without CHX treatment and despite long exposure times with highly sensitive detection reagents. However, in the presence of AAP, VP protein levels remain consistent over all time points of CHX treatment. This is likely because capsids are assembled rapidly in the presence of AAP, and because assembled VP proteins are not susceptible to degradation, a VP band persists.

Given the spectrum of AAP phenotypes observed across the major clades, 9 putative evolutionary intermediates (AncAAVs) to the major AAV serotypes also were tested in order to gain insight into what elements of VP structure either impose the observed requirement for AAP or impart an ability for some VPs to perform these functions independently (Zinn et al., 2015, Cell Rep., 12:1056-68). As with the natural serotypes, a broad range of requirement for AAP was observed for the AAPstop60 AncAAVs (FIG. 3A). See Table 4 for individual AAPstop60, stop20, and AAP rescue vector titration data for FIGS. 3A-3E).

TABLE 4

| | | % WT titers | | |
|---|---|---|---|---|
| | | AAPstop60 | AAPstop20 | AAPstop20 + AAP |
| Trial 1 | Anc113 | 126.757 | −0.030 | 61.254 |
| | Rh32.33 | 52.415 | 96.577 | 114.124 |
| | AAV3 | 27.085 | 0.050 | 61.983 |
| | Anc110 | 20.791 | −0.037 | 34.955 |
| | AAV9 | 23.145 | −0.013 | 28.922 |
| | AAV5 | 22.512 | 6.297 | 83.410 |
| | AAV4 | 5.429 | 5.662 | 54.170 |
| Trial 2 | Anc113 | 253.371 | 0.359 | 46.539 |
| | Rh32.33 | 39.059 | 89.731 | 105.907 |
| | AAV3 | 28.319 | 0.840 | 78.249 |
| | Anc110 | 23.771 | 0.281 | 39.816 |
| | AAV9 | 8.769 | −0.010 | 26.927 |
| | AAV5 | 14.108 | 6.912 | 79.285 |
| | AAV4 | 4.204 | 5.080 | 5.109 |
| Average | Anc113 | 190.064 | 0.165 | 53.897 |
| | Rh32.33 | 45.737 | 93.154 | 110.016 |
| | AAV3 | 27.702 | 0.445 | 70.116 |
| | Anc110 | 22.281 | 0.122 | 37.386 |
| | AAV9 | 15.957 | −0.012 | 27.924 |
| | AAV5 | 18.310 | 6.605 | 81.348 |
| | AAV4 | 4.816 | 5.371 | 29.639 |

Figure 9:
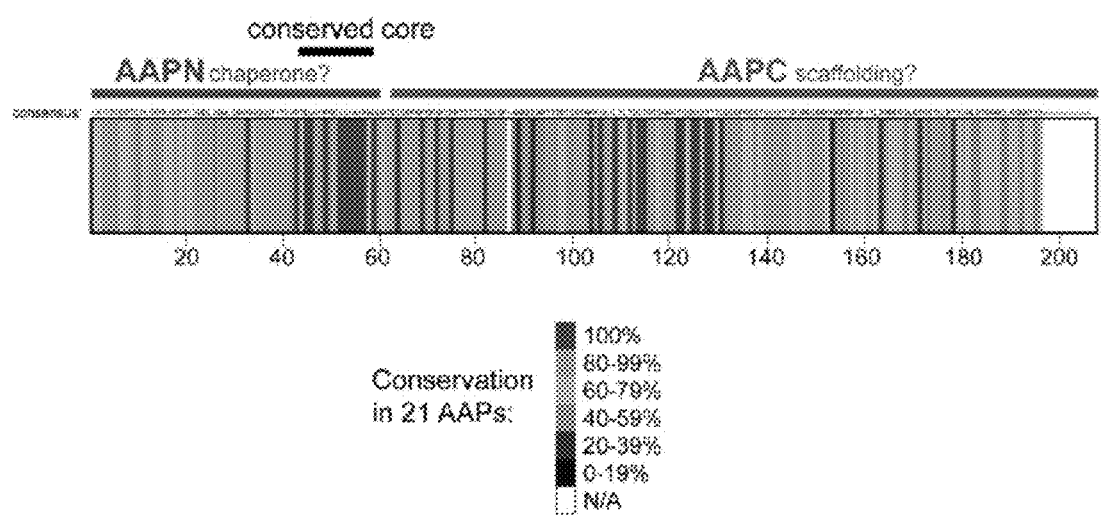
FIG. 9 is a schematic showing the conservation of AAP across 21 serotypes. Related to FIGS. 1A-D, 2A-F, 3, 6, and 7. Multiple protein sequence alignment (ClustalW) for AAPs of all 21 serotypes examined in this study. Ancestral sequence reconstruction to generate the Anc-AAVs (and by extension, Anc-AAPs) is detailed elsewhere (Zinn et al., 2015, Cell Rep., 12:1056-68). In brief, VP coding sequence for AncAAVs was determined first on a protein level, and then reverse translated to DNA for subsequent synthesis using a codon table from the most similar extant AAV sequence available. The conserved core (black bar) identified previously (Naumer et al., 2012, J. Virol., 86:13038-48) retains high conservation across the Anc-AAPs, and may confer the chaperone function suggested by the data for AAPN (purple bar) in the present work. The work described herein additionally points to a scaffolding function for AAP that may be largely contained in the C-terminal two-thirds of AAP (AAPC, grey bar).

Although the AAPstop60 early stop codon is placed upstream of domains shown to be required for AAP2 function, it is downstream of a highly conserved region (residues 52-57) in AAP (FIG. 9, conserved core). This domain was shown by deletion analyses to be important for AAP2 function, but not sufficient to assemble VP3 only capsids without more C-terminal portions of AAP present (Naumer et al., 2012, J. Virol., 86:13038-48). Because AAPs in other serotypes have not yet been tested by deletion analyses, and because algorithms that generated the AncAAVs were applied only to the VP ORF and may have unpredictable consequences on AAP (Zinn et al., 2015, Cell Rep., 12:1056-68), we wanted to examine whether a partially functional, N-terminal AAP (AAPN) was expressed from some AAPstop60 constructs, contributing to the observed varying requirement for AAP across the 21 AAVs that were examined.

For the six AAVs whose AAPstop60 produces at least 10% of WT titer and for AAV4, recently demonstrated to assemble VP3-only capsids without AAP (Earley et al., 2017, J. Virol., 91:e01980-16), further upstream stop constructs (AAPstop20) were generated, placing the early stop codon at residue ~23 in the AAP ORF (silent mutations in VP). Of these, AAV5, rh32.33, and AAV4 AAPstop20 produce virus, while AAV3, AAV9, Anc110, and Anc113 do not (FIG. 3B). Although the B1 antibody does not detect AAV4 and rh32.33, levels of VP protein produced from the remaining AAPstop20 constructs mirror the titer (FIG. 3C).

Taken together with FIGS. 2A-E, these results demonstrate that stability is a serotype-specific property of VP proteins that fall into one of three categories: (i) independently stable, (ii) require only AAPN for stability, or (iii) requiring full-length AAP. These results clearly illustrate a role for AAP in VP stability and provide an explanation for the broad range of requirement for AAP. The discrepancy between AAPstop60 and WT titers, particularly for serotypes requiring only AAPN, points to additional shortcomings in some serotypes' VPs for which AAP compensates, and potentially discrete functions contained primarily in AAPN versus the C-terminal two-thirds of AAP (AAPC).

Taking into consideration VP stability, AAPstop60 titers, and AAPstop20 titers, for clarity, the AAP phenotypes were categorized as (i) AAP-independent, (ii) AAPC-independent, and (iii) AAP-dependent (FIG. 3D). Additionally, it was shown that the AAPC-independent phenotype is a property of the VP proteins and not a result of a fully functional AAPN by demonstrating that AAPN of an AAPC-independent serotype cannot rescue viral production of an AAP-dependent serotype (FIG. 10).

To examine whether serotypes with different AAP phenotypes' VPs are subject to the same mechanisms of degradation, degradation of AAV3 proteins were blocked in the same manner as previously performed for AAV8 (FIG. 8B). Proteasome inhibition with Bortezomib provided a dose-responsive, robust rescue as with AAV8, and E1 inhibition with MLN7243 rescued VP at the highest dose. Unlike AAV8, Inhibiting Lysosomal acidification with Bafilomycin robustly rescued AAV3 VP levels in a dose dependent fashion, indicating that AAPC-independent serotypes (or at least AAV3) may be more susceptible to Lysosomal degradation or autophagy. These results could also suggest that AAPN somehow promotes the proteasome as the primary means of degradation, whether by blocking lysosomal degradation or by other means, because AAPN is present in the AAV8 AAPstop60 lysates but is absent in the AAV3 AAPstop20 lysates.

Example 21—AAPC does not Impact Virion Morphology, Infectivity, or Stability

While AAPN alone facilitates the production of appreciable quantities of virus for many serotypes, whether AAPN-assembled particles retain the proper morphology as well as infectivity functions was next addressed. TEM imaging of AAV3 WT and AAV3AAPstop60 vectors indicate identical gross particle morphologies (FIG. 11A). To examine whether AAPC loss affected infection capabilities, AAV9, AAV3, and their AAPstop60 vectors were tested on HEK293 cells in culture (FIGS. 11B-C), demonstrating that virus assembled without AAPC retain infection capabilities. Additionally, the melting temperature of these particles were tested, and no appreciable difference was observed (FIG. 11D).

Example 22—Requirement for AAP Exhibits Branch Specificity in the Context of a Putative AAV Phylogeny As a next step toward identifying VP structure responsible for assembly functions, an overview of how AAP phenotypes diverge across the wide genetic range of AAV capsids tested was sought, aiming to identify phenotypic differences across small genetic distances. AAP phenotypes of the 12 natural serotypes and the nine ancestral variants were correlated to the reconstructed phylogeny (FIG. 3E). This revealed branch-specific AAP dependence profiles, with phylogenetic nodes illustrating clear divergence in AAP phenotype. Among other apparent trends, Anc80, Anc81, Anc82, Anc83, and Anc84 comprise a fully dependent lineage that terminates in AAV8 and rh. 10, and will thus be referred to as Branch D (FIG. 3E, red arrow). At the Anc82 node, a phenotypic switch from AAP-dependent to AAPC-independent is observed in its successor Anc110. The serotypes that diverge from Anc110, rh8 and AAV9, are also AAPC-independent; this branch was named Branch I (FIG. 3E, green arrow).

Example 22—Phenotype-to-Phylogeny Mapping Analysis Reveals a Set of Residues Functioning in AAPC-Independent Assembly The observation that AAP phenotypes have branch-specific trends within the phylogeny presented the opportunity for a facile method to identify elements of VP structure critical for assembly functions. Given that VP sequence diverges by small increments along each of these branches, it was hypothesized that a set of residues homologous only within the members of their respective branch were likely to functionally contribute to capsid assembly. To this end, a multiple sequence alignment was generated with the Branch D and Branch I members. Within the alignment, a total number of 149 positions varied, however, at only twelve positions, the residue is conserved within Branch I, with a different yet shared identity on Branch D. Of these twelve, eight individual residues and two pairs of adjacent residues comprise 10 sites on VP. At some of these sites, residue identity diverges within Branch I members; however, they share a chemical property that contrasts with Branch D. For example, site 1 is a basic lysine in Branch D serotypes, compared to a threonine in Branch I for Anc110 and rh8, and a serine in AAV9, both hydroxylic residues. The approach to identify a phenotypic switch along a reconstructed phylogeny and then interrogate the conserved differences across the two diverging lineages for the phenotype of interest in order to map the structural determinant(s) responsible was named phenotype-to-phylogeny mapping.

Example 24—A Functional Motif Conferring AAPC-Independent Assembly and VP Protein Stability is Transferable to a Heterologous Capsid To test whether the 10 sites constitute a motif that functions in capsid assembly, the Branch I identities were engrafted onto a member of Branch D and tested to determine whether the resulting hybrid gains AAPC-independent assembly function. Anc82, the node from which Branch I diverges, was chosen as the background for these mutations; as the closest relative to the Branch I serotypes it is more likely to tolerate several targeted mutations and retain functionality than a more distant relative. All ten sites in Anc82 were mutated to Branch I identities en masse by site-directed mutagenesis, creating a variant named 82DI (FIG. 4A). 82DIAAPstop60 gained AAPC-independent assembly function (FIG. 4B). To determine the minimal motif required to confer this phenotype, each site was individually reverted back to its Branch D identity. All revertants are AAP-dependent (FIG. 4C), corroborating the 10 sites identified using phenotype-to-phylogeny mapping not only constitute a functional motif critical for capsid assembly, but also comprise a minimal motif required for AAPC-independent assembly in this subset of serotypes.

Whether this DI motif affects VP protein stability was next assessed. Consistent with other AAP-dependent serotypes (FIG. 2B), Anc82 exhibits a dramatic decrease in VP levels in the AAPstop60 condition, whereas 82DIAAPstop60 does not (FIG. 4D; see Table 5 for individual 82DI single revertant vector titration data.

TABLE 5

| | | \% DI WT titer | | | | | |
| | | Trial 1 | | Trial 2 | | Average | |
| | | WT | AAPstop | WT | AAPstop | WT | AAPstop |
|---|---|---|---|---|---|---|---|
| site | 82DI | 100.000 | 12.047 | 100.000 | 16.941 | 100.00 | 14.494 |
| 1 | S163K | 140.290 | 0.158 | 91.977 | −0.008 | 116.134 | 0.075 |
| 2 | S206A | 128.656 | −0.013 | 56.219 | −0.009 | 92.438 | −0.011 |
| 3 | R478K | 154.220 | −0.035 | 76.595 | −0.008 | 115.408 | −0.022 |
| 4 | V481L | 95.214 | 0.033 | 56.655 | −0.009 | 75.935 | 0.012 |
| 5 | M520V | 7.970 | 0.017 | 0.382 | −0.010 | 4.176 | 0.003 |
| 6 | S528T | 123.339 | −0.064 | 83.723 | −0.019 | 103.531 | −0.042 |
| 7 | H586L | 44.444 | −0.035 | 18.062 | −0.008 | 31.253 | −0.021 |
| 8 | QA592AP | 157.428 | −0.024 | 122.904 | −0.013 | 140.166 | −0.019 |
| 9 | QN599NS | 120.802 | 0.029 | 83.228 | −0.019 | 102.015 | 0.005 |
| 10 | I603A | 110.992 | 0.019 | 90.107 | −0.024 | 100.549 | −0.003 |

To properly categorize 82DI's AAP phenotype, AAPstop20 for Anc82 and DI were generated, and loss of protein in 82DIstop20 was observed, indicating that 82DI is AAPC-independent (FIG. 4D).

To assess the broader impact of AAPC-independent assembly on the capsid as a whole, 82DI's biophysical properties and transduction capabilities was further characterized compared to its parental strain, Anc82. The $T_m$ of 82DI is 5° C. lower than Anc82 (FIG. 4E), a primary indication of a biophysically distinct entity (Pacouret et al., 2017, Mol. Ther., 25:1375-86). Considering the marked changes in Anc82 vs. 82DI's $T_m$ and AAP phenotypes, the infectivity of both variants was tested. 82DI retains infectivity and transduction may be increased moderately compared to Anc82 both in vitro (FIG. 12A) and in vivo (FIGS. 4F & 12B).

Example 25—Candidate Residues Contributing to AAP-Independent Assembly Lie at the VP Trimer Interface To examine how this motif influences particle assembly, where these residues lie within the 3-dimensional fold of VP and within an assembled capsid were mapped. Although crystal structures of AncAAVs are not available, the terminal Branch D (AAV8) and Branch I serotypes (AAV9) have been solved (DiMattia et al., 2012, J. Virol., 86:6947-58; Nam et al., 2007, J. Virol., 81:12260-71), and were used as surrogates to map the DI motif. Two of the 10 sites lie in the unstructured region of the VP N-terminus, but only site 1 is outside of VP3. Of the eight sites within the structured region of VP, seven of them map to the three-fold interface of a VP trimer and contact a neighboring monomer (FIGS. 5A-C).

Comparing an AAV8 (AAP-dependent) trimer to an AAV9 (AAPC-independent) trimer at the atomic level, most of these sites exhibit compelling evidence for stronger inter-monomeric interactions within an AAPC-independent trimer than in the AAP-dependent trimer (FIGS. 5D-F). For example, a conserved glutamic acid forms a salt bridge with an adjacent monomer's histidine at site 7 in the AAV9 trimer that cannot form with the leucine at site 7 in AAV8 (FIG. 5D).

On AAV9, a hydrogen bond forms between a conserved asparagine and a glutamine at site 8 of an adjacent VP monomer. On AAV8, this bond is unable to materialize due to a Gln to Ala substitution (FIG. 5E). Site 10 lies at the 3-fold axis, and beneath a conserved phenylalanine, the valine residues in AAV9 create a much larger network of hydrophobic interactions than the alanines in AAV8 (FIG. 5F). Moreover, the site 10 interaction exists between all three monomers of the trimer simultaneously. These observations suggest that in AAPC-independent serotypes, this motif aids in trimer stabilization and possibly nucleates capsid assembly in the absence of a full length AAP.

Example 26—AAPC-Independent Capsomer Nucleation

Next, it was hypothesized that VPs of AAPC-independent AAVs are able to associate into oligomers in the absence of AAPC, whereas AAP-dependent serotypes' VPs do not strongly associate unless a full-length AAP is present. To test this theory, VP-VP interaction of AAP-dependent and AAPC-independent AAVs were evaluated by co-immunoprecipitation of VP3 with HA-tagged VP1 as bait (FIGS. 6A-B). The AAPC-independent VP1s tested, AAV3 and 82DI, were able to co-precipitate VP3 in the absence of a full-length AAP, despite low VP3 levels in the input. Conversely, neither AAP-dependent AAV2 nor Anc82 VP1 co-precipitated significant VP3 despite appreciable input levels (FIG. 6B).

Addition of AAP2 allowed VP3 co-precipitation in AAP-dependent serotypes, and co-precipitated an unknown VP species between VP2 and VP3's predicted molecular weights in the AAPC-independent serotypes (marked with *, FIG. 6B). These may be VP2-like proteins translated from an alternate start codon, or VP1 N-terminal cleavage/degradation products stabilized by AAP. Despite the appreciable increase in Anc82 and AAV3 VP3 input levels in the +AAP condition, these data support the above hypothesis.

To begin examining whether AAP is promoting oligomerization into species of defined geometry such as trimers or pentamers, or whether the increase in VP-VP interactions observed by co-IP are more randomized associations, cross-linking agents were added to transfected cell lysates and VP species interrogated by Western Blot (FIG. 6C). In the presence of AAP, a single supershifted VP band appears around 97 kDa when DSG (7 angstrom crosslinking arm) was added, and a slightly larger supershifted doublet appears when DSS (11 angstrom crosslinking arm) was added. Although it is difficult to determine the molecular weight of crosslinked species due to unpredictable migration patterns, the discrete banding suggests that AAP promotes VP-VP interactions of defined geometry or number of monomers, but may also be indicative of increased association of VP with a host protein(s) involved in capsid assembly, an association promoted by AAP.

To further ensure that the VP oligomerization process was being interrogated separately from their assembly into full capsids, the IP experiment was repeated with AAV2 VPs, adding rep, aap2, helper, and ITR-flanked reporter genome plasmids in trans to allow quantification of assembled DRPs (FIG. 13A). Appreciable quantities of genomes were detected only in the input and supernatant fractions, but absent from the IP fraction. ELISA to quantify fully assembled capsids mirrored these results (FIG. 13B), indicating only oligomerized VPs were precipitated. Taken together, these data support that in addition to a role for AAP in VP protein stability, AAP also promotes oligomerization of VP proteins to nucleate assembly of the icosahedron, which could potentially increase the efficiency of the capsid assembly process.

OTHER EMBODIMENTS

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

The disclosed methods, compositions, and other materials are disclosed as described herein, but it is understood that combinations, subsets, interactions, groups, etc. of these methods, compositions, and other materials are also disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. An adeno-associated virus (AAV) capsid polypeptide comprising an amino acid sequence having at least 99% sequence identity to the amino acid sequence of SEQ ID NO: 3.

2. The AAV capsid polypeptide of claim 1, having the amino acid sequence of SEQ ID NO:3.

3. The AAV capsid polypeptide of claim 1, encoded by the nucleic acid sequence of SEQ ID NO: 4.

4. A virus particle comprising the adeno-associated virus (AAV) capsid polypeptide of claim 1.

5. The virus particle of claim 4, further comprising a transgene.

6. A nucleic acid molecule comprising a nucleic acid sequence encoding the adeno-associated virus (AAV) capsid polypeptide of claim 1.

7. The nucleic acid molecule of claim 6, having the nucleic acid sequence of SEQ ID NO: 4.

8. The nucleic acid molecule of claim 6, encoding the amino acid sequence of SEQ ID NO: 3.

9. A vector comprising the nucleic acid molecule of claim 6.

10. A host cell comprising the nucleic acid molecule of claim 6.

11. The host cell of claim 10, wherein the host cell is a packaging cell.

12. A packaging cell comprising a nucleic acid molecule encoding the adeno-associated virus (AAV) capsid polypeptide of claim 1.

13. The packaging cell of claim 12, wherein the packaging cell lacks an assembly activating protein (AAP).

14. An AAV capsid polypeptide comprising the amino acid sequence of SEQ ID NO:1 comprising amino acid substitutions K163T, A206S, K478R, L481V, V520M, T528S, L586N, A592Q, P593A, N599H, S600N, and A603V.

* * * * *